US007359062B2

(12) United States Patent
Chen et al.

(10) Patent No.: US 7,359,062 B2
(45) Date of Patent: Apr. 15, 2008

(54) HIGH SPEED SPECTRAL DOMAIN FUNCTIONAL OPTICAL COHERENCE TOMOGRAPHY AND OPTICAL DOPPLER TOMOGRAPHY FOR IN VIVO BLOOD FLOW DYNAMICS AND TISSUE STRUCTURE

(75) Inventors: Zhongping Chen, Irvine, CA (US); Jun Zhang, Irvine, CA (US); J. Stuart Nelson, Laguna Niguel, CA (US)

(73) Assignee: The Regents of the University of California, Oakland, CA (US)

( * ) Notice: Subject to any disclaimer, the term of this patent is extended or adjusted under 35 U.S.C. 154(b) by 273 days.

(21) Appl. No.: 11/009,717

(22) Filed: Dec. 9, 2004

(65) Prior Publication Data

US 2005/0171438 A1    Aug. 4, 2005

Related U.S. Application Data

(60) Provisional application No. 60/528,024, filed on Dec. 9, 2003.

(51) Int. Cl.
*G01B 9/02* (2006.01)
(52) U.S. Cl. .................................... 356/479
(58) Field of Classification Search .............. 356/479, 356/497
See application file for complete search history.

(56) References Cited

U.S. PATENT DOCUMENTS 5,956,355 A * 9/1999 Swanson et al. ............ 356/479
5,991,697 A * 11/1999 Nelson et al. ................ 702/49
6,944,551 B2 * 9/2005 Chen et al. ................... 702/49
7,079,254 B2 * 7/2006 Kane et al. ................. 356/456
2002/0122182 A1 * 9/2002 Everett et al. .............. 356/479
2004/0239938 A1 * 12/2004 Izatt .......................... 356/450
2005/0018201 A1 * 1/2005 de Boer et al. ............. 356/479
2005/0171438 A1 * 8/2005 Chen et al. ................. 600/476

OTHER PUBLICATIONS

Dopler standard deviationimaging for clinical monitoring of in vivo human skin blood flow, Zhao et al, Optics Letters, Aug. 2000, pp. 1358-1360.*
Real-time phase -resolved optical coherence tomography and optical Doppler tomography, Ding et al, Optics Express, Mar. 2002, pp. 236-245.*
Phase-resolved function optical coherence tomography, Ren et al, Optics Letters, Oct. 2002, pp. 1702-1704.*

* cited by examiner

*Primary Examiner*—Samuel A. Turner
(74) *Attorney, Agent, or Firm*—Myers Dawes Andras & Sherman LLP

(57) ABSTRACT

A system for tomographic imaging includes a source of at least partially coherent radiation, a frequency-swept laser source and an interferometer. The radiation in the interferometer is phase modulated at a modulation frequency for elimination of DC and autocorrelation noises as well as the mirror image. The interference fringes of the radiation backscattered from the sample into the interferometer are detected to obtain a spectral signal. The spectral signal of the detected backscattered interference fringes is transformed to obtain a location dependent signal at each pixel location in a data window. A tomographic image of the fluid flow in the data window is generated for display and of the structure of the scanned fluid flow sample in the data window from the location dependent signal is generated.

21 Claims, 9 Drawing Sheets

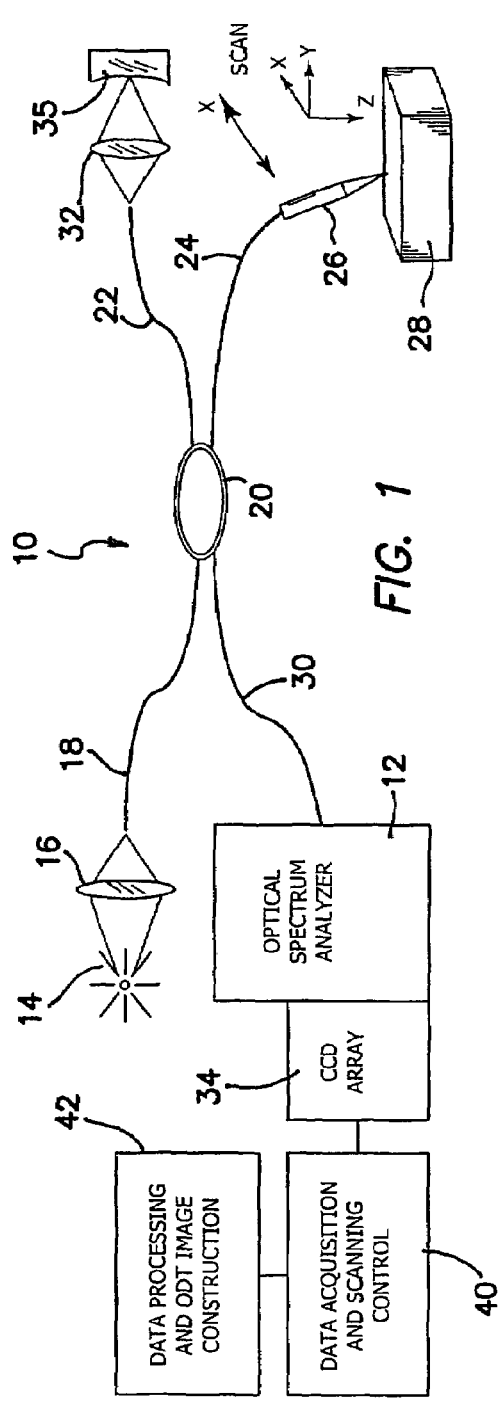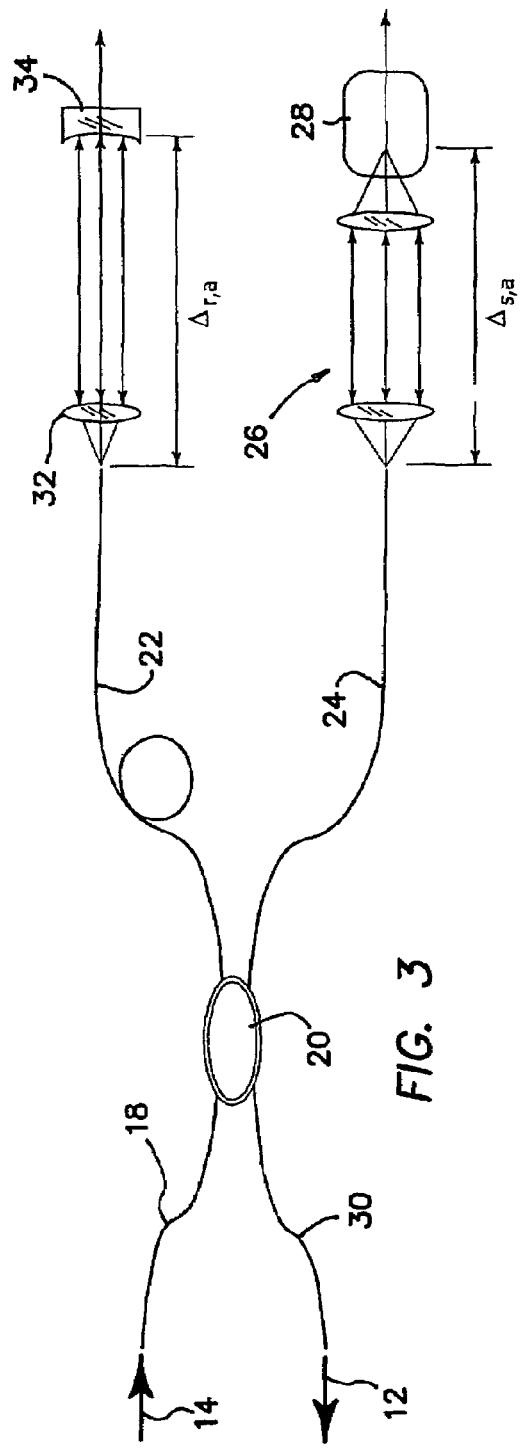
FIG. 1
FIG. 3

HIGH SPEED SPECTRAL DOMAIN FUNCTIONAL OPTICAL COHERENCE TOMOGRAPHY AND OPTICAL DOPPLER TOMOGRAPHY FOR IN VIVO BLOOD FLOW DYNAMICS AND TISSUE STRUCTURE

RELATED APPLICATIONS

The present application is related to U.S. Provisional Patent Application Ser. No. 60/528,024, filed on Dec. 9, 2003, which is incorporated herein by reference and to which priority is claimed pursuant to 35 USC 119.

This invention was made with Government support under Grant Nos. WF23281, GM58785, and Rr01192 awarded by the National Institutes of Health. The Government has certain rights in this invention.

BACKGROUND OF THE INVENTION

1. Field of the Invention

The invention relates to the field of biomedical imaging, and in particular to functional optical coherence tomography and functional optical Doppler tomography.

2. Description of the Prior Art

Direct visualization of physiological anatomy provides important information to the diagnostician and therapist for the evaluation and management of disease. High spatial resolution noninvasive techniques for imaging in vivo blood flow dynamics and tissue structure are currently not available as a diagnostic tool in clinical medicine. Such techniques could have a significant impact for biomedical research and clinical diagnosis. Techniques such as Doppler ultrasound and laser Doppler flowmetry (LDF) are currently used in medical diagnosis for blood flow velocity determination. Doppler ultrasound uses the principle that the frequency of ultrasonic waves backscattered by moving particles are Doppler shifted. However, the relatively long acoustic wavelengths required for deep tissue penetration limits the spatial resolution to approximately 200 µm. Although LDF has been used to measure mean blood perfusion in the peripheral microcirculation, strong optical scattering in biological tissue limits spatially resolved flow measurements by LDF.

Optical Doppler tomography (ODT), also named Doppler optical coherence tomography (Doppler OCT), is capable of measuring microflows using the optical Doppler effect. Early ODT systems were unable to achieve high imaging speed, high velocity sensitivity and high spatial resolution simultaneously. A phase-resolved algorithm was developed in the prior art to obtain high velocity sensitivity while maintaining high imaging speed and high spatial resolution. This technique has been applied to clinical investigations and microfluidic study. To further the study of microflows, a Doppler variance algorithm has been added to the phase-resolved ODT. The Doppler frequency shift depends on the Doppler angle between the probe and the flow direction. By contrast, Doppler variance is less sensitive to Doppler angle and is more efficient for mapping the flows buried in non-transparent media. Currently, ODT systems are implemented in the time domain. Although real-time 2-D flow imaging has been achieved with the time domain ODT, 3-D mapping of complex flows in microfluidic networks requires even higher speed and better sensitivity. In the time domain ODT, mechanical devices are required for axial scanning (A-line scanning) and limit the imaging speed and velocity dynamic range.

Recently, frequency domain F-OCT or FDOCT has shown advantages in imaging speed and signal-to-noise ratio over the time domain OCT. Since the velocity dynamic range of a phase-resolved ODT system is determined by A-line scanning rate, it would be advantageous to extract Doppler information using the frequency domain method. The measurement of flow profiles has been demonstrated using frequency domain method, but the Doppler variance tomography has not been performed in frequency domain.

In Fourier domain OCT (FDOCT) DC and autocorrelation noises decrease the system sensitivity and the mirror image due to the Fourier transformation limits the imaging range of FDOCT. Several methods have been developed to resolve these problems. Phase retrieval algorithms using five interferograms with defined phase relations or a 90° phase shift introduced by translation of the reference mirror were adopted to obtain complex signals to cancel out the autocorrelation noise terms as well as the DC signal. However, these non-instantaneous algorithms require high stability of the systems and limit the imaging speed due to mechanical translation. The phase shift of an N by N (N>2) fiber coupler has been proposed to access the complex image but it has the drawback of phase drift due to temperature sensitivity of the coupler splitting ratio. What is needed is a method which can achieve a full range complex signal to eliminate DC and autocorrelation noises as well as the mirror image.

BRIEF SUMMARY OF THE INVENTION

Optical coherence tomography (OCT) is a noninvasive, noncontact imaging modality that can provide micrometer-scale cross-sectional images of tissue microstructure. The high resolution (~10 µm) of OCT enables real-time, in situ visualization of tissue microstructure without the need to excise and process the specimen as required for conventional biopsy and histopathology. Conventional OCT, which bases on a scanning optical delay line, is defined as time domain OCT (TDOCT). The different OCT approach of the invention, i.e. Fourier domain OCT (FDOCT) also known as spectral domain OCT or frequency domain OCT and referenced as such throughout this specification, has attracted much attention because of the advantages of higher sensitivity and imaging speed. Throughout this specification and claims the terms "functional OCT", is to be understood as including "OCT", "Doppler OCT", "polarization sensitive OCT", "spectral OCT" and "spectroscopic OCT" unless otherwise specifically indicated by the context to refer to a different methodologies. The technique has the potential for ultrahigh speed and ultrahigh resolution FDOCT in biomedical imaging. In addition to the morphological structural image, FDOCT can also provide functional information of tissue physiology such as blood flow velocity and birefringence adopting Doppler and polarization-sensitive techniques.

Doppler OCT, also named optical Doppler tomography (ODT), combines the Doppler principle with OCT to obtain high resolution tomographic images of tissue structure and blood flow simultaneously. Polarization-sensitive optical coherence tomography (PS-OCT) combines polarization sensitive detection with OCT to determine tissue birefringence that is not discernible using existing optical methods.

A method is described to increase the speed and sensitivity of optical Doppler tomography (or Doppler Optical coherence tomography) by measuring the OCT signal in the spectral (Fourier) domain. The invention can be used for imaging blood flow for ocular diseases, cancer diagnosis, burn depth determination and many other clinic applications involving blood flow.

It is accomplished by two methods. First, instead of scanning the reference mirror and measuring the time dependent interference fringe, the reference mirror is fixed and the full or at least a portion of the spectrum of the fringe signal is acquired. The more of the full spectrum which is obtained, the better will be the resolution of the structure and the velocity images. Once the spectral signal is obtained, the time (or location) dependent fringe signal can be recovered by Fourier transformation of the spectral signal. Once the time dependent signal is determined, the Doppler shift and variance is determined by a phase resolved method using cross correlation algorithm or wavelet analysis. Because the spectral signal represents the signal over the full depth, the sensitivity is increased. Furthermore, spectral signal is acquired in parallel, which can significantly increase the imaging speed.

Second, a spectral signal can also be acquired by scanning the laser wavelength and using a single detector. In the past, the time domain signal was acquired when the reference arm is scanned. The disadvantage is that only the coherence gated area of the signal is acquired. Therefore, both signal sensitivity and imaging speed is limited. Because the spectral signal represents the signal over the full depth, sensitivity is increased. Furthermore, the spectral signal is acquired in parallel, which can significantly increase the imaging speed.

The invention is also directed to frequency domain phase-resolved optical Doppler tomography (FDOCT) with Doppler variance imaging capability. It is disclosed below that utilizing the frequency domain method, phase-resolved FDOCT can achieve much higher imaging speed and velocity dynamic range than the time domain method. In the illustrated embodiment structural, Doppler and Doppler variance images of fluid flow through glass channels are quantified and blood flow through vessels are demonstrated in vivo. What is illustrated is a frequency domain Doppler tomography system with Doppler variance imaging capability using phase-resolved algorithm to measure fluid flows through glass channels and blood vessels.

A swept source based polarization-sensitive Fourier domain optical coherence tomography (FDOCT) system is disclosed that can acquire the Stokes vectors, polarization diversity intensity and birefringence images in biological tissue by reconstruction of both the amplitude and phase terms of the interference signal. The Stokes vectors of the reflected and backscattered light from the sample are determined by processing the analytical complex fringe signals from two perpendicular polarization-detection channels. Conventional time domain OCT (TDOCT) and spectrometer based FDOCT systems are limited by the fact that the input polarization states are wavelength dependent. The swept source based FDOCT system overcomes this limitation and allows accurate setting of the input polarization states. From the Stokes vectors for two different input polarization states, the polarization diversity intensity and birefringence images are obtained.

The disclosed swept laser based Fourier domain optical coherence tomography (FDOCT) system has an imaging range which was doubled by cancellation of the mirror image. The elimination of low frequency noises due to DC and autocorrelation terms increased the system sensitivity by 20 dB.

While the apparatus and method has or will be described for the sake of grammatical fluidity with functional expla-
nations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 1 is a schematic diagram of a high speed Fourier domain F-OCT instrument.

FIG. 3 is a diagram of the reference and sample paths of the interferometer.

FIG. 5d is a velocity profile along the depth at the center of channel (indicated by an arrowed line in FIG. 5b. Circles denote measured values and the line is a parabolic fitting. The image size is 0.75 mm×0.95 mm with a channel dimension of 0.5 mm.

FIGS. 7a and 7b are structure images of skin tissues; FIGS. 7c and 7d are velocity images of blood flows; FIGS. 7e and 7f are velocity variance images of blood flows. The imaging range is 2.5 mm×2.2 mm.

FIG. 12a is the Stokes vector images corresponding to the two input polarization states; FIG. 12b is a polarization diversity intensity image; and FIG. 12c is a phase retardation image.

Figure 2:
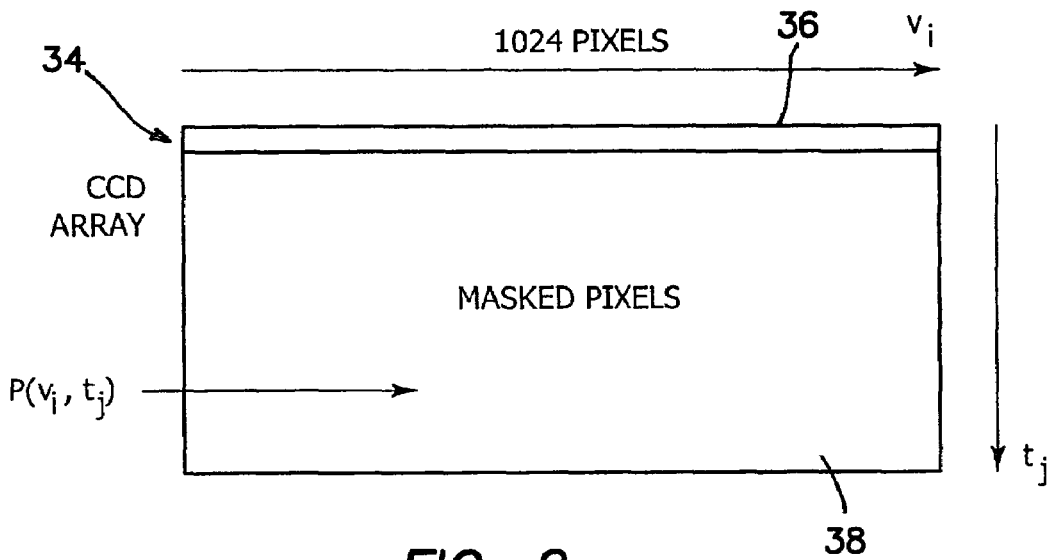
FIG. 2 is a schematic side cross-sectional view of a high speed spectral CCD array.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Although high resolution ODT structural and velocity images of static and moving constituents in turbid samples have been obtained using a time domain instrument, clinical application of the technique requires higher imaging speed. The invention is directed to a high speed FDOCT system for imaging in vivo blood flow. This is achieved and demonstrated according to the approach of the invention by using an FDOCT system based on spectral interferometry, an imaging construction algorithm, Monte Carlo simulation of multiple scattering and coherence gating to gain insight into and provide a model for the FDOCT imaging process.

The prior temporal domain ODT instrument acquires data for each pixel serially by a sequential two-dimensional scan, which limits imaging speed. Image acquisition time for our prototype device is given by $T=N_x N_z \Delta t_p$, where $N_x$ and $N_z$ are the number of pixels in the lateral and depth dimensions, and $\Delta t_p$ is the pixel acquisition time. Inasmuch as detection of the Doppler shift requires sampling the interference fringe intensity over at least one oscillation cycle, pixel acquisition time varies inversely with $\Delta f_D$ (i.e., $\Delta t_p \approx 1/\Delta f_D$). Given a minimum detectable Doppler shift ($\Delta f_D$ (min)), ODT velocity resolution ($v_{ODT}$(min)) is:

$$a. \quad v_{ODT}(MIN) = \frac{\Delta f_D(\min) \lambda_0}{2\bar{n} \cos \theta}$$

Thus, pixel acquisition time is limited not only by detector sensitivity, but also by velocity resolution. For $v_{ODT}$(min) =100 μm/s and $\theta$=70°, $\Delta f_D$ (min)=112 Hz or $\Delta t_p$=9 ms. Therefore, to achieve velocity resolution of 100 μm/s, minimum pixel acquisition time is approximately 9 ms. In a two-dimensional scanning approach, an ODT image of 100×100 pixels requires a minimum acquisition time of 90 s. Imaging speed in the time-domain instrument is limited because temporal interference fringe intensity data used to construct ODT structural and velocity images is acquired serially.

For real-time imaging of static and moving constituents in a turbid sample, the high speed FDOCT system of FIG. 1 based on spectral interferometry is used, which acquires data for FDOCT structural and velocity images in parallel by using an optical spectrum analyzer 12 at the interferometer output to measure time variation of spectral interference fringe intensity ($P_{ODT}(V, t)$). The Michelson interferometer 10 and is a conventional fiber optic interferometer 10 having a low coherence source 14 coupled by optics 16 into source fiber 18 terminating in 2×2 optic splitter 20. Reference fiber arm 22 is coupled through optics 32 to a reference mirror 35. Optic splitter 20 is also coupled to sample fiber arm 24 and terminates in a scanning probe 26 which illuminates and receives backscattered signals from sample 28. The backscattered interference signal is returned through splitter 20 to output fiber arm 30 to analyzer 12. Many other optical components well known to optical interferometry may be included in interferometer 10, which has been described here in abbreviated form only to provide a general context.

Optical spectral interferometry has previously been used for ranging and structural imaging. In spectral interferometry, modulation of the interference fringe intensity in the spectral domain, P(v), is used to determine the locations of all scattering objects along the beam propagation direction. Spectral interferometry is equivalent to coherence gating, and the complex valued analytic signal representations of spectral (P(v)) and temporal ($\Gamma(\tau)$) interference fringe intensity are Fourier transform pairs. Measurement of P(v) can be used to determine $\Gamma(\tau)$, where $\tau$ is related to the path length delay ($\Delta=c\,t$) between light in the sample and reference arms.

Spectral FDOCT measures the time variation of spectral interference fringe intensity ($P_{ODT}(v, t)$). The positions of scattering constituents along the beam propagation axes can be determined by an inverse Fourier transformation of the optical spectrum. The velocity of the moving particles can be determined from the oscillation frequency of the optical spectrum in the time domain. Thus, for each position of the sample probe 26, measurement of $P_{ODT}(v, t)$ by an optical spectrum analyzer 12 allows parallel acquisition of position and velocity information over $N_z$ pixels. Because the entire spectrum of interference fringe intensity is acquired simultaneously with a detector array 34, image acquisition time is reduced to $T=N_x \Delta t_p$ using spectral FDOCT. An FDOCT image of 100 lateral pixels with velocity resolution of 100 μm/s can be acquired in less than a second. Thus, spectral FDOCT allows a two-dimensional image to be acquired with single lateral scan, which reduces image acquisition time by a factor of $N_z$ as compared to the prototype FDOCT system described above. Because no mechanical movement is necessary to probe deeper positions when using an optical spectrum analyzer 12, measurement of the time variation of spectral interference fringe intensity allows rapid imaging of static and moving constituents in the turbid-fluid flow sample 26.

Optical spectrum analyzer 12 with a fast CCD detector array 34 is used to acquire the time variation of spectral interference fringe intensity. Successful development of spectral FDOCT requires design, construction, and integration of a number of system components. The primary tasks to provide such a system include: (1) signal to noise ratio analysis and optimization of system design; (2) development of a high power low coherence source 14; (3) development of an optical spectrum analyzer 12 with high speed detector array 34 and system integration.

Consider first the high power low coherence source 12. Because of the parallel nature of the data acquisition process in spectral interferometry, a high power low coherence source 14 is required to achieve adequate signal to noise ratio for imaging in vivo blood flow. We use a high power low coherence light source 14 using a p-n diode single-pass semiconductor optical amplifier to generate broadband amplified spontaneous emission. The p-n diode is a single GaAs quantum well in an AlGaAs heterostructure with antireflection coatings at both ends. Optical power exceeding 200 mW coupled into a single mode fiber has been previously demonstrated. Collimated seed light emitted by a broad band source is coupled into the input facet (4 μm) of the optical amplifier. A Faraday isolator is used to eliminate the reflected light from the optical amplifier coupled back into the seed light. Emission from the output end of the optical amplifier is collimated and coupled into a single mode fiber. In comparison to alternative high power partially coherent sources (e.g., femtosecond lasers), the smooth noise-free power spectral density profile of the disclosed source is well suited for FDOCT.

Measurement of spectral interference fringe intensity for imaging in vivo blood flow in highly scattering biological tissue requires a spectrum analyzer 12 with a high speed linear detector array 34. The required number of pixels in the array 34 is determined by the resolution ($\Delta v$) of the optical spectrum analyzer 12 and is directly related to the maximum depth ($\Delta_{max}$) that may be interrogated in the turbid fluid flow sample, $$a. \quad \Delta_{max} = \frac{1}{4n} \frac{c}{\Delta v} = \frac{1}{4n} \frac{\lambda^2}{\Delta \lambda} \qquad (1)$$

$\Delta_{max}$ may be interpreted as a coherence length of a virtual source with spectral width $\Delta v$. To image static and moving constituents in a turbid sample at depths to $\Delta_{max}$=2 mm, a spectral resolution of $\Delta v$=27 GHz ($\Delta \lambda$=0.06 nm at center wavelength of 815 nm) is required. Detection of $P_{ODT}(v, t)$ over the power spectral density of the high power low coherence source 14 (i.e., 50 nm) requires a linear detector array with 1024 pixels. Measurement of the Doppler frequency shift ($\Delta f_D$) of blood flow with velocity 1-4 mm/sec and $\theta$=70°, requires a 10 kHz linear array frame rate. To record spectral interference fringe intensity in the spatially-filtered optical spectrum analyzer 12, we use a high speed digital CCD linear detector array 34 (1024×1024 pixels) designed for spectroscopic studies of chemical reactions as diagrammatically depicted in FIG. 2. In the operation of the linear array 34, a solitary row 36 (1024 pixels) of photodetectors is active while remaining rows 38 are masked for image storage and transfer. Low noise high speed linear frame rates are achieved by shifting acquired spectra to successive masked rows 38. More than 256 spectra may be acquired in a single burst at rates up to 300 kHz. Using the high speed CCD linear detector array 34 in burst mode, lateral scans are performed by recording CCD 256 spectra (10 kHz) at each lateral position. These spectra are then read out with a high speed A/D converter included as part of data acquisition and scanning control 40 in FIG. 1 before moving to the next lateral position. Readout time for the full 256 spectra is 300 ms for a 1 MHz 16 bit A/D converter. Use of a 12-bit 25 MHz A/D converter allows an FDOCT velocity image (100×512 pixels) to be acquired in one second. The design and development of the spectrometer 12 is guided by the spectral resolution (0.06 nm), full spectral range (50 nm), pixel size of the CCD array 34, and optimization of the signal to noise ratio.

In the time-domain interferometer temporal interference fringe intensity ($\Gamma_{ODT}(\tau)$) was recorded and FDOCT images of static and moving constituents in a turbid sample were obtained by computing a discrete spectrogram of the temporal interference fringe intensity ($\Gamma_{ODT}(\tau_i, f_j)$). Consider now a conversion algorithm that calculates temporal interference fringe intensity from spectral interference fringe intensity, and then applies the time-frequency representation for FDOCT image construction.

To illustrate the connection between FDOCT spectral ($P_{ODT}(v)$) and temporal ($\Gamma_{ODT}(\tau)$) interference fringe intensity, we consider the correlation between light amplitudes in reference paths 22 and sample paths 24 of interferometer 10 as diagrammatically shown in FIG. 3. The amplitude of light (U(t)) from the partially coherent source 14 which is coupled into the interferometer 10 at time t is written as an harmonic superposition, $$a. \quad U(t) = \int_0^\infty \overline{U}(v) e^{2\pi i v t} dv \qquad (2)$$

where U(t) is a complex-valued analytic signal of a stochastic process representing the field amplitude emitted by a partially coherent light source; $\overline{U}(v)$ is the corresponding spectral amplitude at optical frequency v. Because the stochastic process is stationary, cross spectral density of $\overline{U}(v)$ satisfies equation (3), $$\langle \overline{U}^*(v)\overline{U}(v') \rangle = S_0(v)\delta(v-v') \qquad (3)$$

Here $\langle * \rangle$ is an ensemble average over various realizations of $\overline{U}(v)$; $S_0(v)$ is the source power spectral density in W/Hz and $\delta(v)$ is the Dirac delta function. Light emitted by the partially coherent source 14 is coupled into an optical fiber 18 and split equally into reference path 22 and sample path 24 spectral amplitudes, each denoted by $\overline{U}_0(v)$. After splitting, spectral amplitude of light in the reference path 22 propagates forward to the mirror 35, is reflected, and coupled back into the optical fiber 22. After return to the 2×2 splitter 20, the reference spectral amplitude, $$\overline{U}_r(v) = e^{2\pi i v(2\Lambda_{r,f} n_f(v) + 2\Delta_{r,\alpha})/c} K_r e^{i\alpha_r} \overline{U}_0(v) \qquad (4)$$

Here, n(v) is the optical fiber refractive index; $2\Lambda_{r,f} n_f(v)$ and $2\Delta_{r,\alpha}$ are the round trip optical path lengths in the interferometer reference arm 18 through fiber 34 and air, respectively; $K_r e^{i\alpha_r}$ is the reference mirror amplitude reflection coefficient. After splitting, spectral amplitude of light in the interferometer sample path 24 propagates forward to the turbid sample 28, is backscattered, Doppler shifted, and coupled back into the optical fiber 24. After return to the 2×2 splitter 20, the sample spectral amplitude is, $$\overline{U}_s(v) = e^{2\pi i v(2\Lambda_{s,f} n_f(v) + 2\Delta_{s,\alpha})/c} K_s e^{i\Phi_s(v)} \overline{U}_0(v) \qquad (5)$$

Here, $2\Lambda_{s,f} n_f(v)$ and $2\Delta_{s,\alpha}$ are the round trip optical path lengths in the sample arm 20 through filter and medium; $K_s e^{i\Phi_s(v)}$ is the amplitude reflection coefficient of light backscattered from the turbid sample and coupled back into the optical fiber. Using expressions for the spectral amplitude of light in reference (Eq. 4) path 22 and sample (Eq. 5) path 24, we derive the spectral ($P_{ODT}(v)$) and temporal ($\Gamma_{ODT}(\tau)$) interference fringe intensities. Total power ($P_d$, [W]) detected by the optical spectrum analyzer 12 summed over all frequencies (i.e., wavelengths) is a time-average of the squared light amplitude, $$P_d = \langle |U_s(t) + U_r(t)|^2 \rangle \qquad (6)$$

Combining harmonic expansions (Eq. 2) for $U_s(t)$ and $U_r(t)$ and applying Eq. 3 when computing a time-average, total power detected by the optical spectrum analyzer 12 ($P_d$) is a sum (Eq. 7) of three terms representing reference $P_r(v)$, and sample $P_s(v)$ power densities, and the spectral interference fringe intensity $P_{ODT}(v)$, $$P_d = \int_0^\infty (P_r(v) + P_s(v) + P_{ODT}(v)) dv \qquad (7)$$

$$a. \quad P_s(v) = S_0(v)|K_s(v)|^2 \qquad (8)$$

$$P_{ODT}(v) = 2S_0(v) K_r(v) K_s(v) \cos[4\pi v \Delta_d / c + \varphi_s(v) - \alpha_r] \qquad (9)$$

where $\Delta_d$ determines the phase delay between light traveled in sample arm 24 and reference arm 22. For light backscattered from a static structure $\Delta_d$ is equal to the optical path difference $\Delta$:

$$\Delta_d = \Delta = n_f(v)(\Delta_{s,f} - \Delta_{r,f}) + (\Delta_{r,\alpha} - \Delta_{s,\alpha}) \quad (10)$$

Light scattering from a moving particle is equivalent to a moving phase front, therefore $\Delta_d$ for light scattering from a moving particle can be written as:

$$\Delta_d = \Delta + \bar{n} v_{0z} t \quad (11)$$

where $v_{0z}$ is the velocity of a moving particle along the light propagation axis. To simplify the computation, we assume $\Phi_s$ and $\alpha_r$ is constant over the source spectrum and can be neglected, $P_{ODT}(v)$ is simplified to:

$$P_{ODT}(v) = 2S_0(v) K_r(v) K_s(v) \cos[4\pi v (\Delta + \bar{n} v_{0z} t)/c] \quad (12)$$

Equation 12 shows that $P_{ODT}(V)$ contains information of both location and velocity of moving particles. Important features of $P_{ODT}(V)$ for imaging static and moving structure include: 1) spectral interference fringe intensity of single backscattered light from the static particle ($v_{0z}=0$) is a sinusoidal modulation of the power spectral density ($S_0(v)$) with period, $c/2\Delta$; here $2\Delta$ is the optical path length difference between the static structure and reference mirror. 2) a moving particle in the sample path 24 results in a oscillation of the modulated power spectral at the Doppler frequency $\Delta f_D = 2v_0 \, n \, v_{0z}/c$. Measurement of time variation of spectral interference fringe intensity allows determination of both position and velocity of the moving particle.

If the time delay ($\tau$) between light in reference and sample paths is increased (e.g., by translating the mirror or stretching the optical fiber as in our prototype instrument, total power ($P_d(\tau)$, [W]) detected at the interferometer output by a photo receiver is given by a time-average of the squared light amplitude, $$a. \; P_d = \langle |U_s(t) + U_r(t-\tau)|^2 \rangle \quad (13)$$

Combining harmonic expansions (Eq. 10) for $U_s(t)$ and $U_r(t-\tau)$ and applying Eq. 3 when computing a time-average, total power detected by the photoreceiver ($P_d(\tau)$) at time delay, $\tau$, is a sum (Eq. 14) of three terms representing reference ($I_r$), sample ($I_s$), and temporal interference fringe intensity ($\Gamma_{ODT}(\tau)$).

$$P_d(\tau) = I_r + I_s + \Gamma_{ODT}(\tau) \quad (14)$$

where $\Gamma_{ODT}(\tau)$ is $$\Gamma_{ODT}(v) = 2K_r \int_0^\infty S_0(v) K_s(v) \cos[4\pi v \Delta_d / c + \varphi_s(v) - \alpha_r - 2\pi v \tau] \, dv \quad (15)$$

A comparison of Eqs. 9 and 15 indicates spectral and temporal interference fringe intensity are Fourier transform pairs, a conversion algorithm may be applied to determine $\Gamma_{ODT}(\tau)$ from $P_{ODT}(v)$.

If the zero optical path length is set at the surface of tissue to be imaged, $\Gamma_{ODT}(-\tau)$ is zero for $t > 0$. Temporal interference $\Gamma_{ODT}(\tau)$ can be determined from measured spectral interference fringe $P_{ODT}(v)$.

In order to determine both the phase and amplitude of the interference fringe, digital Fourier transformation or optical Fourier transformation will be used to obtain the complex valued analytic fringe signal $\hat{\Gamma}(\tau)$. Once the complex valued fringe signal is determined, the Doppler shift and variance can be determined by either phase resolved signal processing method, or wavelet analysis methods.

Consider FDOCT image construction using phase resolved method with cross correlations: The Doppler frequency shift ($f_n$) and standard deviation ($\sigma_n$) values at the nth pixel can be calculated with complex analytical signals from the sequential fringe signal determined from the spectral data:

$$f_n = \frac{1}{2\pi T} \tan^{-1} \left( \frac{\text{Im}\left[ \sum_{m=(n-1)M}^{nM} \sum_{j=1}^{4} \tilde{\Gamma}_j(\tau_m) \tilde{\Gamma}_{j+1}^*(\tau_m) \right]}{\text{Re}\left[ \sum_{m=(n-1)M}^{nM} \sum_{j=1}^{4} \tilde{\Gamma}_j(\tau_m) \tilde{\Gamma}_{j+1}^*(\tau_m) \right]} \right) \quad (16)$$

$$\sigma^2 = \frac{1}{2\pi^2 T^2} \left( 1 - \frac{\left| \sum_{m=(n-1)M}^{nM} \sum_{j=1}^{4} \tilde{\Gamma}_j(\tau_m) \tilde{\Gamma}_{j+1}^*(\tau_m) \right|}{\frac{1}{2} \sum_{m=(n-1)M}^{nM} \sum_{j=1}^{4} \left[ \tilde{\Gamma}_j(\tau_m) \tilde{\Gamma}_j^*(\tau_m) + \tilde{\Gamma}_{j+1}(\tau_m) \tilde{\Gamma}_{j+1}^*(\tau_m) \right]} \right) \quad (17)$$

where $\tilde{\Gamma}_j(\tau_m)$ and $\tilde{\Gamma}^*_j(\tau_m)$ are the complex signals corresponding to the jth fringe signal and its conjugate, respectively, $\tilde{\Gamma}_{j+1}(\tau_m)$ and $\tilde{\Gamma}^*_{j+1}(\tau_m)$ are the complex signals corresponding to the next fringe signal and its conjugate, respectively, T is the time duration between sequential fringe data (frame rate of the spectral data), and M is an even number that denotes the window size in the axial direction for each pixel. The calculated Doppler frequency shifts and standard deviation values are then averaged to obtain the Doppler shift and variance images. The velocity sensitivity of phase resolved spectral FDOCT can be as sensitive as 10 µm/s, and the dynamic range can be as high as 300 mm/s if the capture rate of the spectral data is on the order of 300,000/s.

The Doppler flow image in phase-resolved FDOCT is very sensitive to any environmental disturbances such as sample stability. However, because we are interested in the relative motion of blood flow with respect to the tissue, motion artifacts will be corrected by choosing the tissue as a stable reference point for phase measurement.

FDOCT image construction can also be realized using a time-frequency representation. A time-frequency representation (TFR) of a fluctuating signal is a two-dimensional function that characterizes the temporal localization of the spectral energy content. Example TFR's include, short-time Fourier transform, wavelet transform, spectrogram, and the generalized Wigner distribution. FDOCT imaging can also be constructed using a time-frequency analysis such as wavelet transformation and centroid of the power spectrum.

Consider further the embodiment of the invention as illustrated in a system and method for frequency domain phase-resolved optical Doppler and Doppler variance tomography. The schematic of the frequency domain FDOCT system is diagrammatically shown in FIG. 1. The dispersed spectrum is sampled by a photon detector array 34. With an object 28 placed in the sample arm 24 and with two optical paths matched, an interference pattern will be generated on the detector array 34. The frequency domain representation of the interference pattern or intensity, I(k), is described by:

$$I(k) = S(k) \left[ 1 + \int_0^\infty \int_0^\infty a(z) a(z') \exp[-2kn(z - z')] dz dz' + 2 \int_0^\infty a(z) \cos(2knz) dz \right] \quad (18)$$

where k is the wave number, S(k) is the spectral intensity distribution of the light source, n is the refractive index, z is the distance measured from the plane where the optical path difference between the reference and sample arms is zero, a(z) denotes the backscattering amplitude of the sample. The first term in equation (18) is a constant. The second term is the mutual interference of all elementary waves. The first and second term together give the DC components in the time domain. The third term in equation (18) encodes the backscattering amplitude information of the sample. An inverse Fourier transform of the third term in equation (18) gives a complex signal $\tilde{I}(z)$, containing amplitude and phase information of the interference signal in time domain. Furthermore, $\tilde{I}(z)$ can be written as:

$$\tilde{I}(z)=\tilde{I}(Z)e^{j\phi(Z)} \quad (19)$$

where $\Phi(z)$ is the phasor of f(z).

When there is a moving object passing through the sample volume 28, there is an equivalent phase front, $\Delta z = nV \cdot k$, adding to z, where n and V are the refractive index of sample and the velocity of the moving object, respectively. The equivalent phase shift will introduce a phase change on $\tilde{I}(z)$, which is the Doppler effect. The corresponding Doppler shift can be estimated by comparing the phasors between two complex signals during two exposures at a same location. Namely, the phase change is recorded by the product of $\tilde{I}_0(z)$ and $\tilde{I}^*(z)$, where * denote the conjugate operation and T is the time interval between two exposures and T determines the A-line scanning rate. This calculation is integrated for a certain time duration in order to get a better signal-to-noise ratio. The Doppler shift is obtained using equation (20):

$$f_D = \frac{\Delta\phi(z)}{2\pi T} = \frac{\text{argument}\left(\frac{1}{N}\sum_{j=1}^{N}\tilde{I}_{jT}(z)\cdot\tilde{I}^*_{(j+1)T}(z)\right)}{2\pi T} \quad (20)$$

where N is the number of A-lines used for averaging. From equation (20), two features of phase-resolved FDOCT can be inferred. First, T determines the Doppler frequency shift range, namely, the velocity dynamic range because $\Delta\Phi(z)$ can only be correctly traced between $-\pi$ and $\pi$. Second, T determines the imaging speed. Since no A-line scanning is required in frequency domain, a large velocity dynamical range and an extremely high imaging speed are possible using frequency domain method. Therefore, frequency domain FDOCT is capable of imaging and quantifying ultra-fast flow dynamics.

In addition to the local velocity information, phase-resolved FDOCT system gives the variance of local velocity, which is given by:

$$\sigma^2 = \frac{\int (\omega-\bar{\omega})^2 P(\omega)d\omega}{\int P(\omega)d\omega} \quad (21)$$

$$= \frac{1}{T^2}\left\{1 - \frac{\left|\frac{1}{N}\sum_{j=1}^{N}\tilde{I}_{jT}(z)\cdot\tilde{I}^*_{(j+1)T}(z)\right|}{\frac{1}{N}\sum_{j=1}^{N}\tilde{I}_{jT}(z)\cdot\tilde{I}^*_{jT}(z)}\right\}$$

where $P(\omega)$ is the power spectrum of Doppler frequency shift and $\bar{\omega}$ is the average Doppler frequency shift. The value of $\sigma^2$ depends on the flow velocity distribution. Variations of flow velocity broaden the Doppler-frequency spectrum and result in a larger $\sigma^2$. Thus, the Doppler variance image obtained by phase-resolved FDOCT system can be an indicator of flow variations and can be used to study flow turbulences. The computation of phase change and Doppler variance using equations (20) and (21) is shown in the flowchart of FIG. 4 where IFT is the inverse Fourier transform, | | is the absolute value.

Figure 4:
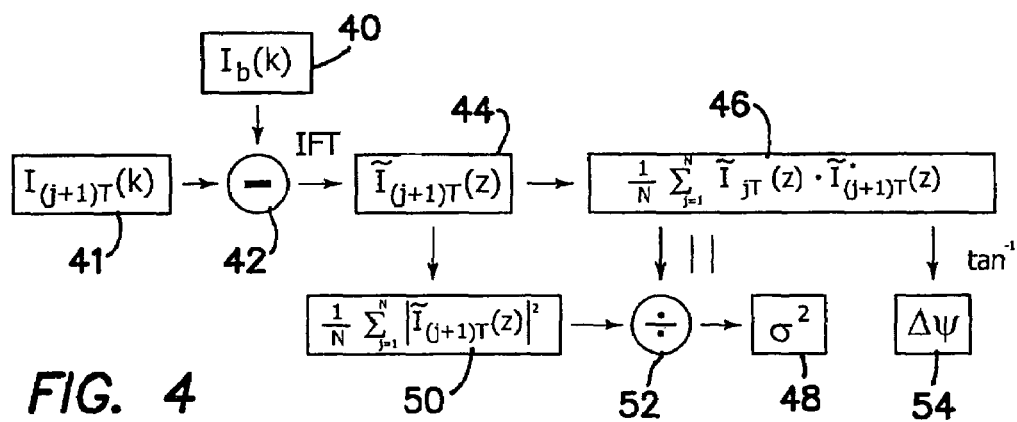
FIG. 4 is a flowchart of the computation of phase change and Doppler variance according to the invention.

FIG. 4 shows a signal-processing flow chart of the phase-resolved frequency domain FDOCT system of FIG. 1. A background light ($I_b(k)$) from reference arm 22 is recorded in advance of data collection at step 40. The $I_b(k)$ is subtracted from I(k) at step 42 in order to reduce the DC component in the time domain. After inversely Fourier transformed at step 44, cross-correlation between sequential A-line is calculated at step 46. In our experiments, 10 cross-correlations are used for an average. Other numbers of cross-correlations can be chosen according to design preference. Both Doppler shift and variance are calculated from the cross-correlation using equations (20) and (21) at step 54 and steps 48-52 respectively.

A super-luminescent diode 14 (SLD) with a spectrum centered at 1315 nm and a total delivered power of 8 mW was used. The back-reflected light from the reference arm 22 and the sample arm 24 was dispersed over a 1×512 InGaAs detector array 34 by a 300 mm imaging spectrograph 12. The total wavelength range spreading on the detector array 34 was 109.7 nm, corresponding to a spectral resolution of 0.21 nm and an imaging depth of 2.2 mm in vacuum. The resulting axial resolution is about 10 μm. The exposure time for each A-line collection was set to 30 μs and the time for data transferring was 530 μs. Thus, the A-line rate we achieved was about 1800 Hz, which gave a velocity dynamic range of 6.0 mm/s at a Doppler angle of 84°. The acquired data was linearized in k space to make the data uniformly sampled. Doppler shift was converted to velocity and the Doppler variance was normalized.

Figure 5A:
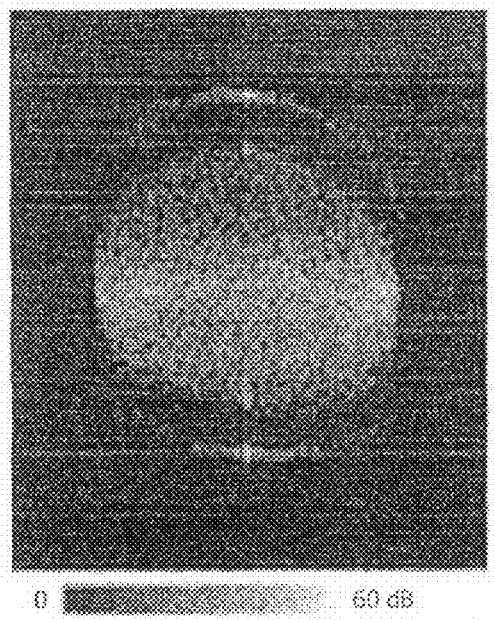
FIGS. 5a-5d are phase-resolved Doppler images. A structural image is shown in FIG. 5a, a velocity image in FIG. 5b and a normalized Doppler variance image of a fluid flow in FIG. 5c.
Figure 5B:
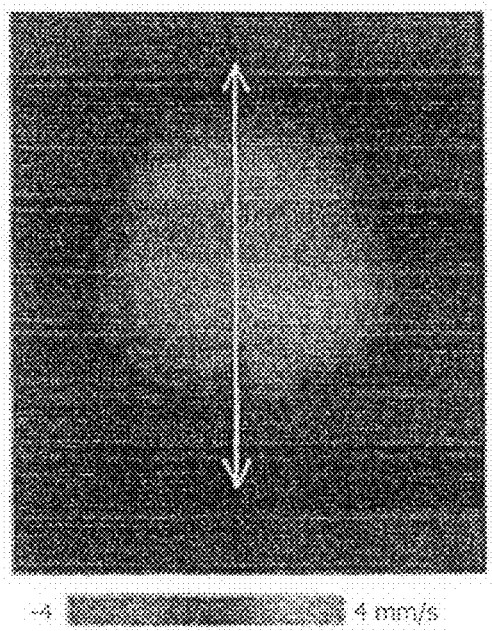
Figure 5C:
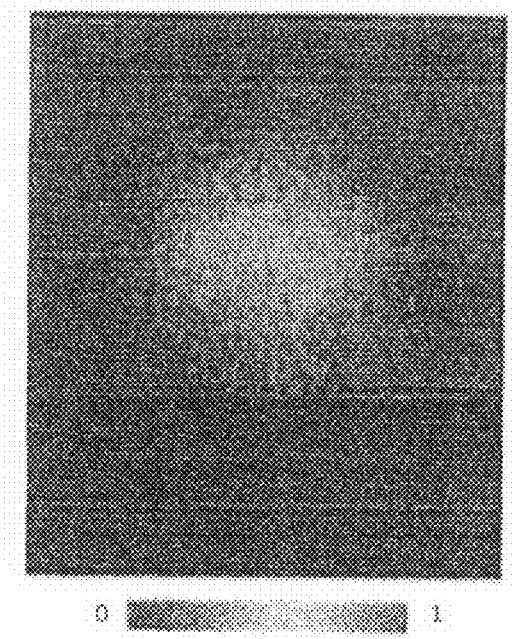
Figure 5D:
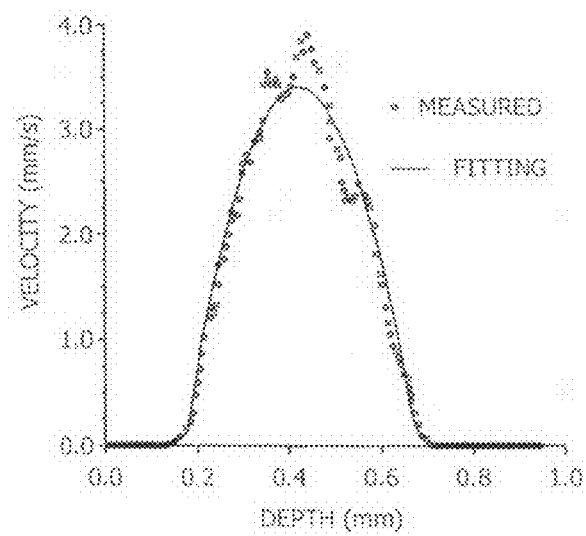

FIGS. 5*a*-5*c* show the structural, velocity and Doppler variance images respectively of a scattering fluid flowing through a glass channel. The imaging size is 0.75 mm by 0.95 mm. A polystyrene bead solution (mean diameter: 0.3 μm, volume concentration: 0.26%) was used as working fluid. The fluid was driven through a glass channel (outer diameter: 700 μm; inner diameter: 500 μm) by a syringe pump. For this experiment, the fluid was pumped into the glass channel at a rate of 20 μl/min, corresponding to an average flow velocity of 1.70 mm/s within the glass channel. FIG. 5*a* shows the structural image of the glass channel with polystyrene beads. FIG. 5*b* is the velocity image of the flowing fluid. The Doppler angle was set to 86.2°. The velocity was color-coded into red and blue to represent two opposite directions. The presence of different velocities (property of pressure driven flow) within the glass channel was observed. The average velocity measured by the phase-resolved FDOCT system was 1.66 mm/s. The difference between the measured value and pumped value was within 2.5%. FIG. 5*c* shows the normalized Doppler variance image that gives the variation of the fluid velocity distribution. FIG. 5*d* is the velocity profile along the depth at the center of the channel, indicated by an arrowed line in FIG. 5*b*. The profile has a parabolic shape, which reflects the property of pressure-driven flow, as expected.

Figure 6:
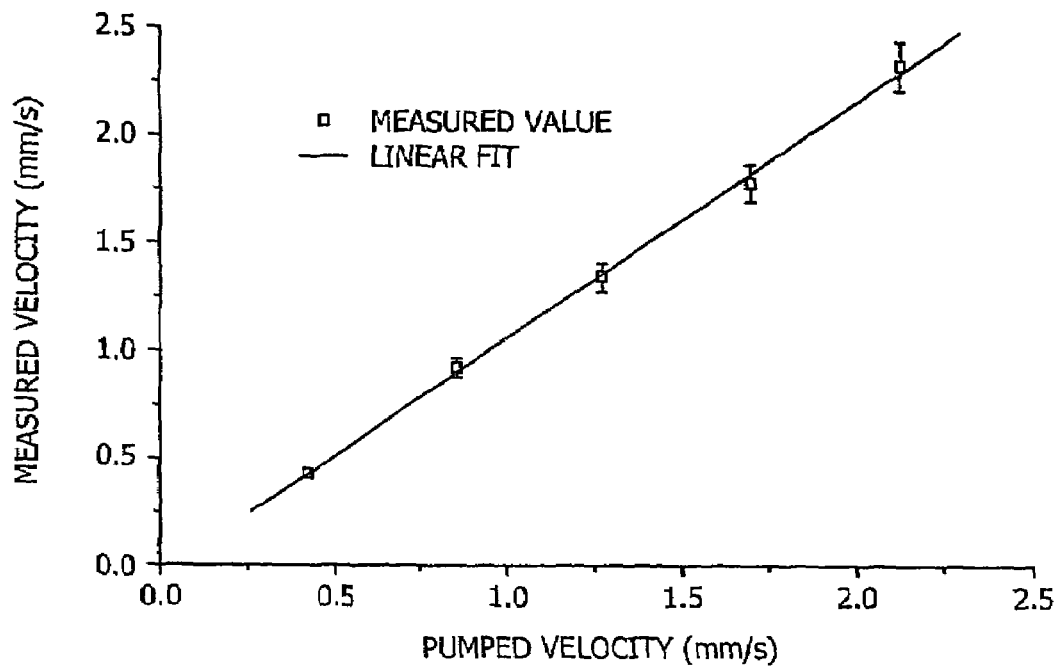
FIG. 6 is a graph of measured average velocity vs. pumped average velocity. Solid squares denote the measured values and the line is a linear fitting. The error bars show 5% error between fitted and measured values.

Flows of the polystyrene bead solution pumped at different velocities were used to test the measurement linearity of the system. The fluid was driven through the same glass channel by a syringe pump. FIG. 6 shows the measured average velocities as a function of pumped average velocities. Solid squares and line denote the measured values and the linear fitting respectively. The error bar shows 5% error between measured and fitted values. The measured average velocity increased with the increasing of the pumped velocity, as expected.

Figure 7A:
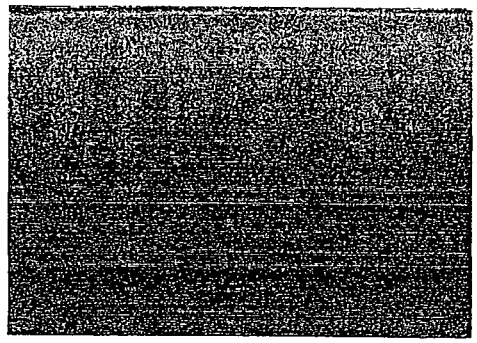
FIGS. 7a-7f show Doppler and Doppler variance measurements of human finger skin tissues.
Figure 7B:
Figure 7C:
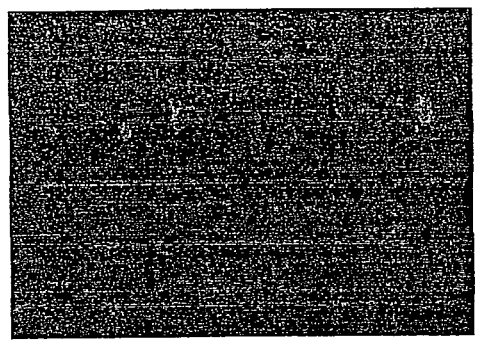
Figure 7D:
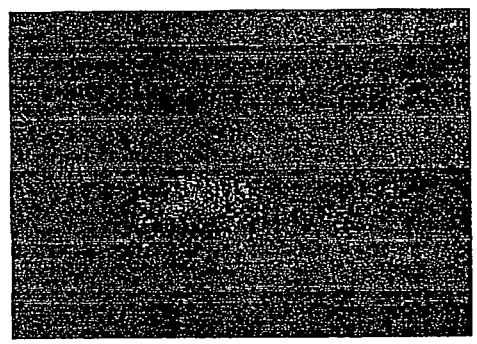
Figure 7E:
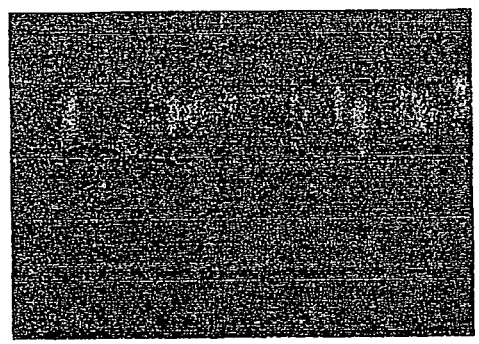
Figure 7F:
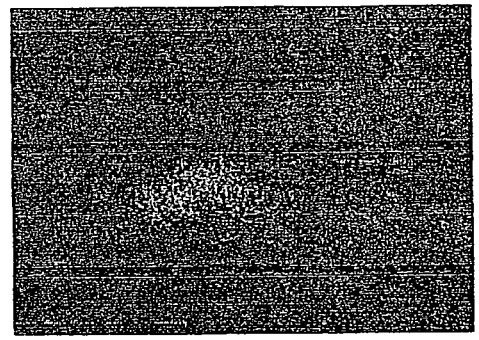

FIGS. 7a-7c show the structural, velocity and velocity variance images of human finger skin tissues. In FIGS. 7a, 7c, and 7e images were taken from the back of a finger, and the images of FIGS. 7b, 7d, and 7f were taken from the tissue next to the nail. The imaging range was 2.5 mm (width) by 2.2 mm (depth). The structure of finger skin was clearly shown in images FIGS. 7a and 7b. Although the blood vessels were visible (FIGS. 7c and 7d), Doppler variance images provide a much better mapping of blood vessels (FIGS. 7e and 7f). The results indicate that it is much easier to identify the blood vessels in the Doppler variance images than in the velocity images. Since the orientation of flows buried in non-transparent media cannot be reliably acquired in advance, the Doppler variance images provide a much more accurate mapping of the location of vessels.

As described above, the imaging speed and velocity dynamic range of a phase-resolved FDOCT system are limited by A-line rate. On the other hand, high A-line rate can also reduce the phase noise caused by environmental vibrations. In frequency domain FDOCT, no A-scanning is required and only the time between exposures limits the A-line rate. Therefore, the frequency domain method improves the performance of phase-resolved FDOCT. Ultra-high speed spectrometer with 30 KHz spectral acquisition rates is currently available; if such a high speed spectrometer were used, a frame rate as high as 30 frames/s can be achieved with a velocity dynamic range of 100 mm/s at a Doppler angle of 84°. This would allow for imaging of ultra-fast flow dynamics within complex microfluidic networks, which cannot be accessed by other techniques. In addition, a Doppler variance algorithm was also demonstrated for mapping blood vessels in frequency domain. Its advantage for efficiently locating flows buried in non-transparent media was shown.

In summary, what is disclosed is a frequency domain phase-resolved FDOCT system, which incorporates Doppler variance imaging capability. This technique is capable of imaging fluid flows through microchannel and blood vessels in vivo. The methodology of the invention is capable of achieving much faster imaging speed than the time domain ODT. Given its noninvasive nature, high signal-to-noise ratio, and high speed and simple hardware setup, frequency domain phase-resolved FDOCT is promising for real-time applications, such as imaging and quantifying fast microflow dynamics.

Figure 8:
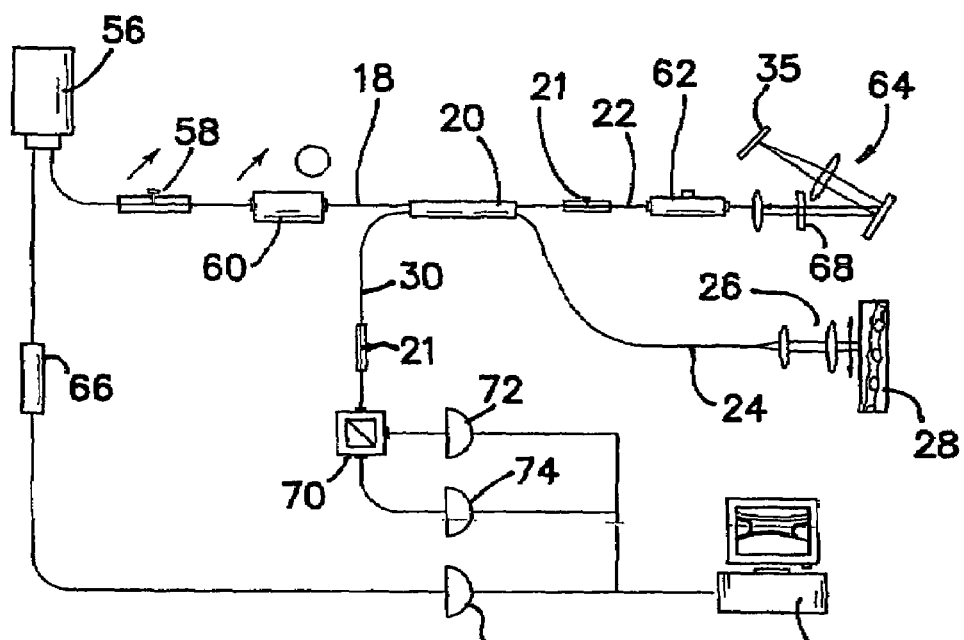
FIG. 8 is a schematic of the FDOCT system of the invention.

In another embodiment, a swept laser source 56 as shown in the diagram of FIG. 8 is employed. A 1310 nm swept laser (Micron Optics) 56 with a FWHM bandwidth of 85 nm and output power of 5 mW is operated at the sweeping rate of 500 Hz. The output light is polarized to 45° with respect to the optical axis of the crystal in the polarization modulator (New Focus) 60. The polarization modulator 60 is driven by a two step drive function to generate a phase shift of zero and π/2 at 250 Hz. The corresponding two Stokes vectors of the output light are orthogonal in the Poincare sphere so that the birefringence measurements are independent of the orientation of the optical axis in the sample. Subsequently, the light is split into reference arm 22 and sample arm 24 by a 2x2 coupler 20. A polarization controller 21 in arms 22 and 30 provide for polarization stability or control. In the reference arm 22, a polarizing electro-optical (EO) phase modulator (JDS Uniphase) 62 is used to generate a stable carrier frequency of 1 MHz for elimination of the mirror image and low frequency noise. The EQ phase modulator 62 is driven by a ramp waveform with 40 MHz sampling rate. To match dispersion caused by the EQ phase modulator 62, an optical setup 64 similar to a rapid scanning optical delay line with a stationary mirror 35 is adopted which can compensate the group velocity dispersion. Calculations showed that the higher order dispersion can be neglected in our system. The reference power is attenuated by an adjustable neutral density attenuator 68 for maximum sensitivity. As shown in FIG. 8 5% of the laser output is split and propagated through a 100 GHz fiber Fabry-Perot (FFP) interferometer (Micron Optics) 66 to generate comb signals coupled through photodetector 76 to data acquisition board 78 for dynamic calibration of the swept wave number function that is essential for rigorous conversion from time to wave number space. In the detection arm 30, the interfered beam is split into two polarization channels by a polarization beam splitter (PBS) 70. The fringe signals from the two polarization channels are detected by two photodetectors 72 and 74 and then converted by a 12 bit data acquisition board 78 sampling at 10 MHz.

Figure 10:
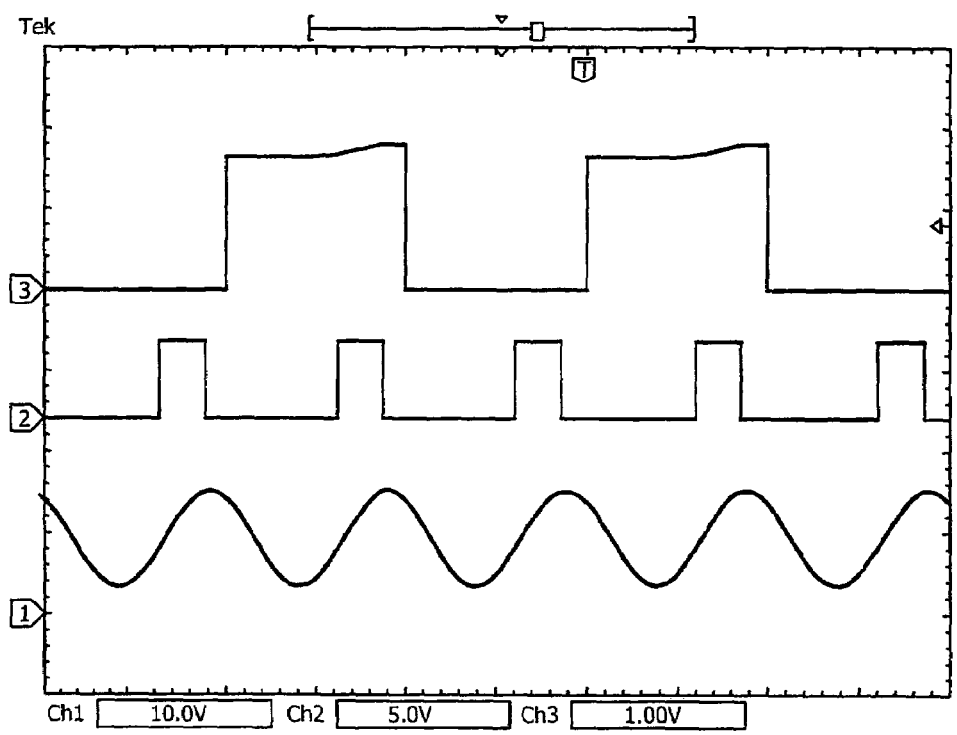
FIG. 10 is a synchronizing time clock diagram for the FDOCT system of FIG. 8. Channel 1 is the sinusoidal signal to drive the swept source. Channel 2 is the signal used to trigger data acquisition. Channel 3 is the drive signal to control the polarization modulator.

The synchronizing time clock diagram of the system of FIG. 8 is shown in FIG. 10. Since the half wave voltage of the polarization modulator is proportional to the working wavelength, the phase shift and the corresponding polarization state would be wavelength dependent with a constant driven voltage. Assuming a Gaussian spectrum light source with the FWHM bandwidth of $\Delta\lambda$ and center wavelength $\lambda_o$, an average polychromatic phase error of $\Delta\phi=\phi_o\Delta\lambda/(\sqrt{8\ln2}\lambda_o)$ would be introduced, where $\phi_o$ represents the phase shift at center wavelength. The swept source provides the advantage of controlling the phase shift during wavelength sweeping. In our system, drive signals of the polarization modulator were carefully calibrated according to the swept spectra function to obtain a constant phase shift across the total spectrum. With $\lambda_o$=1310 nm and $\Delta\lambda$=85 nm, a 2.8% or 2.5° average polychromatic phase error was corrected for the phase shift of $\lambda/2$. The phase correction for the current system is not significant because of the limited source bandwidth used. However, in the case of a high resolution system with a broadband light source, the polychromatic phase error cannot be neglected and this correction will be essential for accurate quantification of polarization properties of biological tissues.

Figure 9:
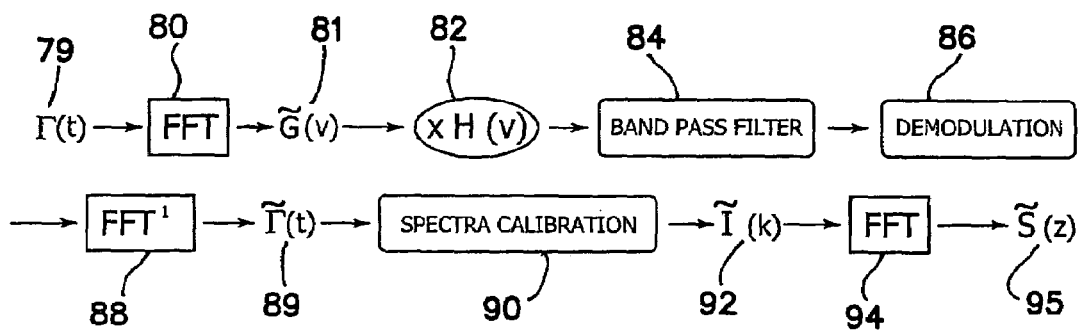
FIG. 9 is a block diagram of the algorithm by which the time fringe signal is converted into the complex analytical depth encoded signal of the system of FIG. 8.

The complex analytical depth encoded signal $\tilde{S}(z)$ is converted from the time fringe signal $\Gamma(t)$ by the digital approach shown in the block diagram of FIG. 9, where FFT denotes the fast Fourier transform as step 80, × is a multiplying symbol, H(v) is the Heaviside function at step 82 given by:

$$H(v) = \begin{cases} 0 & v < 0 \\ 1 & v \geq 0 \end{cases} \quad (22)$$

and FFT$^{-1}$ at step 88 denotes the inverse fast Fourier transform. The time fringe signal $\Gamma(t)$ is first transformed from time to frequency space by FFT at step 80. Multiplication of H(v) at step 82 selects the positive term of the Fourier transformed signal. The signal is then bandpass filtered at step 84 with a 400 kHz bandwidth filter to remove the low frequency and DC noises. The subsequent demodulation step 86 shifts the center frequency of the filtered interference term from 1 MHz to zero. The frequency fringe signal is then converted back at step 88 to time space by inverse FFT. To cancel the distortion originating from the nonlinearities in the wave number function k(t), the data was numerically remapped at step 92 from uniform time to uniform wave number space based on the function of k(t) which is determined by the spectra calibration process described previously. The last FFT step 94 performed in k space retrieved the complex depth encoded fringe signal $\tilde{S}(z)=A(z)e^{i\phi(z)}$ which contains both the amplitude A(z) and phase φ(z) terms. From the amplitude information, the structure image can be acquired. Doppler mean frequency and Doppler standard deviation images are reconstructed by comparing the phase term between sequential scans. The birefringence image is calculated from the phase and amplitude information of the signals from both polarization channels. The measured sensitivity enhancement is about 20 dB after cancellation of the autocorrelation and DC noises. The imaging range was doubled from 2 mm to 4 mm with removal of the mirror image.

From the complex signals of the two orthogonal channels, the Stokes vector for the axial pixel z and one polarization state can be calculated as:

$$I(z)=\tilde{S}_H(z)\tilde{S}^*_H(z)+\tilde{S}_V(z)\tilde{S}^*_V(z)$$

$$Q(z)=\tilde{S}_H(z)\tilde{S}^*_H(z)-\tilde{S}_V(z)\tilde{S}^*_V(z)$$

$$U(z)=2Re[\tilde{S}^*_H(z)\tilde{S}_V(z)] \quad (2)$$

$$V(z)=2Im[\tilde{S}^*_H(z)\tilde{S}_V(z)]$$

where I, Q, U and V are the four components of the Stokes vector. $\tilde{S}_H(z)$ and $\tilde{S}_V(z)$ are the complex signals from the horizontal and vertical polarization channels at axial pixel z, respectively, $\tilde{S}^*_H(z)$ and $\tilde{S}^*_V(z)$ are their conjugates, respectively. From the Stokes vectors for the two polarization states, the polarization diversity intensity image was obtained by averaging the two I. To determine the birefringence image, the detected signal reflected from the surface of the sample was adopted as the reference. The phase retardation was calculated by comparing the Stokes vectors between the surface and deeper axial position.

Figure 11:
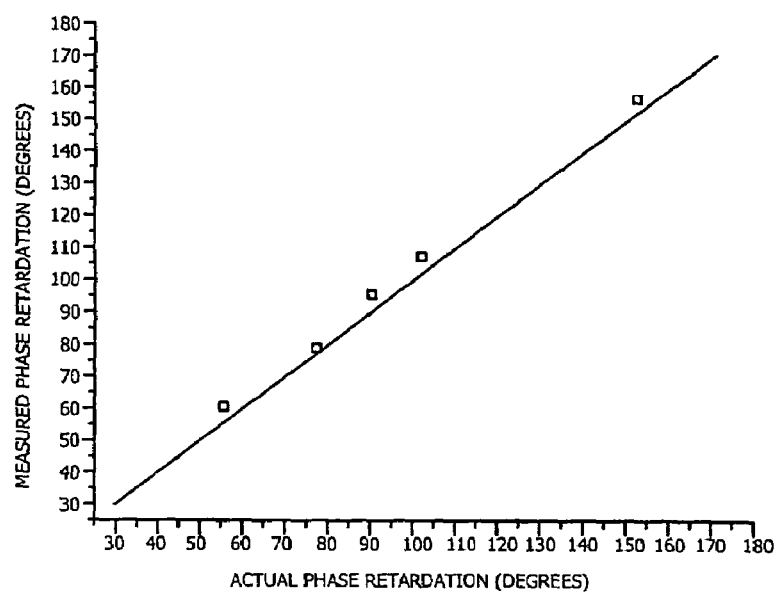
FIG. 11 is a graph of the measured phase retardation versus actual phase retardation for different wave plates in the system of FIG. 8. The round-trip retardation values of the wave plates for measurement are 55.5°, 77°, 90°, 101.6° and 151.9°, respectively. The solid line represents the actual phase retardation and the points represent the measured phase retardation.

To evaluate the system and processing method of FIGS. 8-10, standard wave plates with different retardation (Casix, Inc.) were used as samples 26. The retardation values of these wave plates were previously calibrated using a polarimeter (Thorlabs). For each wave plate, 200 A scans were averaged to determine the phase retardation values which are presented in FIG. 11. The average error of the measured phase retardation compared with calibrated values was 4.5° and the average standard deviation was 4.1° which demonstrates that the experimental data are in good agreement with expected theoretical values. The measured result is similar to those reported with TDOCT systems.

Figure 12A:
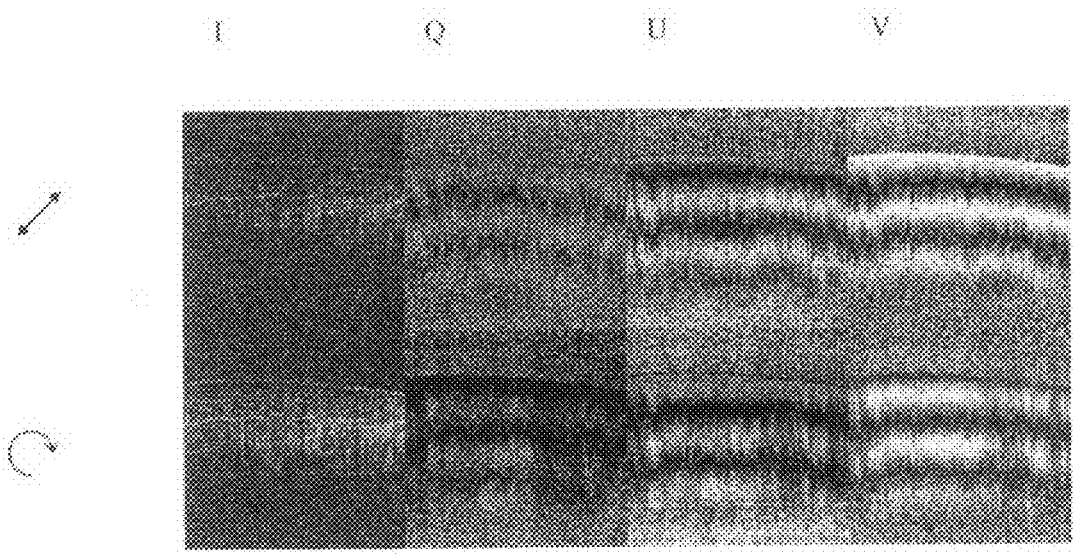
FIGS. 12a-12c are images of the Stokes vectors, polarization diversity intensity and phase retardation in rabbit tendon.
Figure 12B:
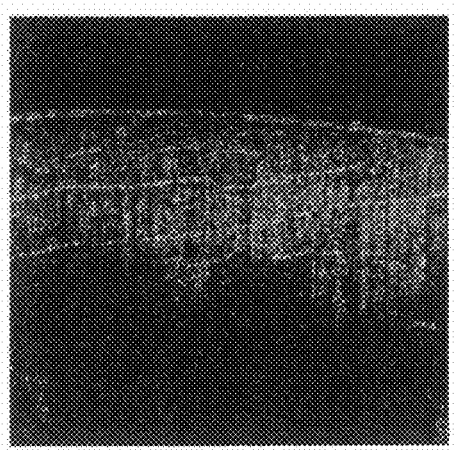
Figure 12C:
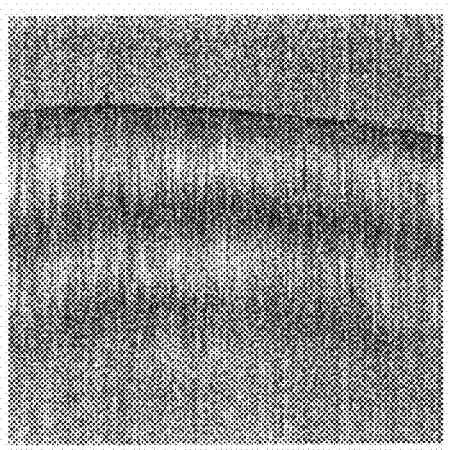

To illustrate the performance of the system of FIG. 8 in biological tissues, rabbit tendon was imaged. The simultaneous imaging of the Stokes vectors, polarization diversity intensity and birefringence is shown in FIGS. 12a-12c. The imaged area is 4×3.9 mm with the zero distance difference set in the center of the depth scale. The top four panels of FIG. 12a are the Stokes vectors corresponding to the two different polarization states. The bottom panel images are polarization diversity intensity in FIG. 12b and phase retardation in FIG. 12c images.

Thus, it can now be understood that in the embodiment of FIG. 8 a fiber based polarization-sensitive FDOCT system was demonstrated. The Stokes vectors, polarization diversity intensity and birefringence images in biological tissue were obtained by processing the analytical complex fringe signals from two polarization channels.

FDOCT has the advantages of higher sensitivity and imaging speed. However, DC and autocorrelation noises decrease the system sensitivity and the mirror image due to the Fourier transformation limits of the imaging range of FDOCT. The obscure object structure and phase error due to these parasitic terms compromise the reconstruction of complex fringe signals. The disclosed synchronous method using a phase modulator 62 in a swept laser based FDOCT system achieves a full range complex signal to eliminate DC and autocorrelation noises as well as the mirror image. The structure, blood velocity and birefringence information of biological tissue can be acquired from the complex signal.

Consider now in more detail how the mirror image is removed. In the case of a swept source based FDOCT system of FIG. 8, where the wave number k is a function of time k=k(t), the fringe signal can be converted from time to frequency space by the Fourier transform. Because the maximum depth range of OCT imaging is limited due to the strong attenuation of light with depth in tissue, the corresponding frequency functions of the interference and autocorrelation terms are also limited. By choosing an appropriate carrier frequency, the negative and positive frequency terms of the interference signal can be separated from each other and from the low frequency noise which is not affected by the carrier frequency. Thus, the DC and autocorrelation noises as well as the mirror image can be eliminated.

In a FDOCT system, the detected intensity can be expressed as:

$$I(k) = S(k)R_R + \qquad (23)$$

$$S(k)\int_{-\infty}^{+\infty}\int_{-\infty}^{+\infty}\sqrt{R_S(\Delta z)R_S(\Delta z')}\,e^{i[k(\Delta z-\Delta z')+\phi(\Delta z)-\phi(\Delta z')]}d\Delta z d\Delta z' +$$

$$2S(k)\sqrt{R_R}\int_{-\infty}^{\infty}\sqrt{R_S(\Delta z)}\cos[k\Delta z+\phi(\Delta z)]d\Delta z$$

where k is the wavenumber, S(k) is the spectral density of the laser source, $R_R$ and $R_S$ are the reflectivities of reference and sample arms, respectively, Δz and Δz' denote the double pass path length difference between sample and reference arms, and φ is the phase shift. The first term in Eq. (23) represents the reflected intensity from the reference mirror. The second autocorrelation term is the mutual interference of all elementary waves in the sample under study. These two terms yield the DC and low frequency noises which obscure the structure of the tissue under study. From the last interference term in Eq.(23), the depth information of the sample can be obtained by Fourier transformation from k to z space. Since the Fourier transformation of a real function is Hermitian, the structure term is always accompanied by a mirror image. This can be illustrated by the Fourier transformation of a simple co-sinusoidal interference term $$\cos(k\Delta z)\xrightarrow{FT}\frac{1}{2}[\delta(z-\Delta z)+\delta(z+\Delta z)] \qquad (24)$$

In the case of a swept laser based FDOCT system, where the wave number k is a function of time k=k(t), the fringe signal can also be converted from time to frequency space by Fourier transformation. Because the maximum depth range of OCT imaging is limited due to the strong attenuation of light with depth in tissue, the corresponding frequency functions of the interference and autocorrelation terms are also limited as long as the wave number is scanned smoothly. Thus by choosing an appropriate carrier frequency, the negative and positive terms of the Fourier transformed interference signal can be separated from each other and from the low frequency noise which is not affected by the carrier frequency but due to DC and autocorrelation terms. The needed carrier frequency can be estimated as a distance shift in z space. For simplicity, a linearly swept laser source, i.e. $k=k_0-mt$, was adopted for the estimation. The co-sinusoidal interference term can be written as $$\cos(k\Delta z - \Omega t) = \cos\left[k\left(\Delta z + \frac{\Omega}{m}\right) - \frac{\Omega k_o}{m}\right] \quad (25)$$
$$= \cos\left[k(\Delta z + z_o) - \frac{\Omega k_o}{m}\right] \stackrel{FT}{\rightarrow}$$
$$\frac{1}{2}\left[\delta(z - \Delta z - z_o)e^{i\frac{\Omega k_o}{m}} + \delta(z + \Delta z + z_o)e^{-i\frac{\Omega k_o}{m}}\right]$$

Where $\Omega$ is the angular carrier frequency and $z_0=\Omega/m$ is the corresponding double pass distance shift. Compared with Eq. (24), the negative and positive terms of the Fourier transformed interference signal are separated by a generated distance of $2z_0$. Therefore, the image can be constructed from only the positive (or negative) term.

Figure 14:
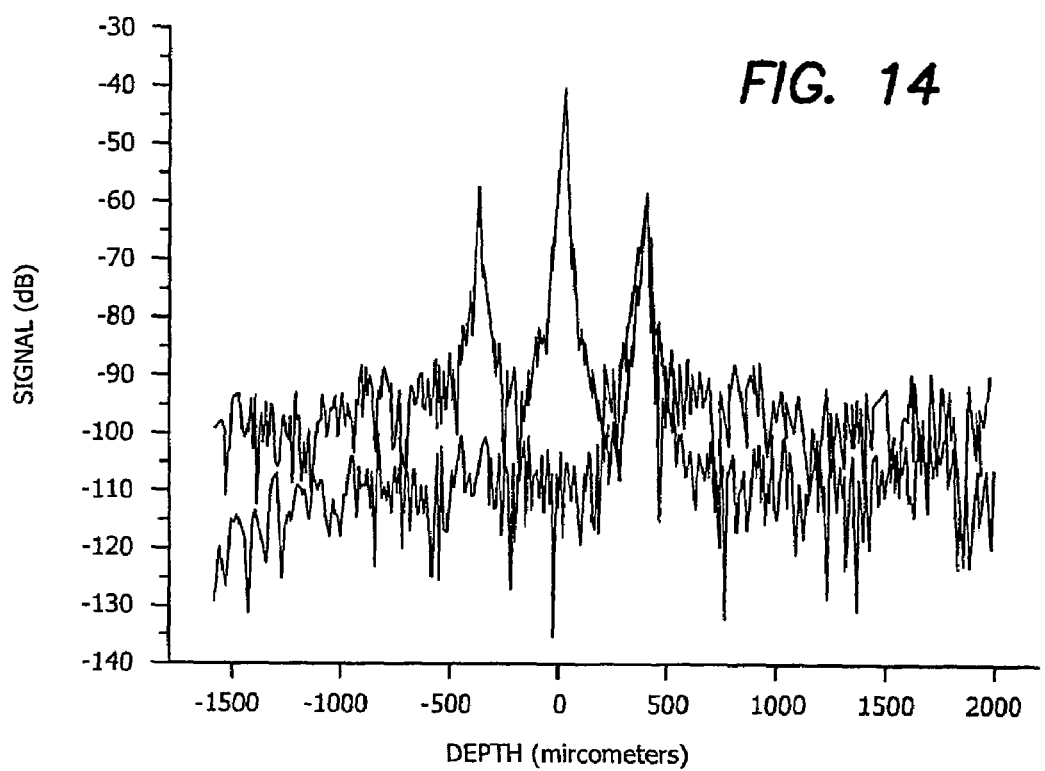
FIG. 14 is a graph of the sensitivities measured with a −57.6 dB reflector. The upper line is the sensitivities without an EO phase modulator and the lower line is with an EO phase modulator.
Figure 13A:
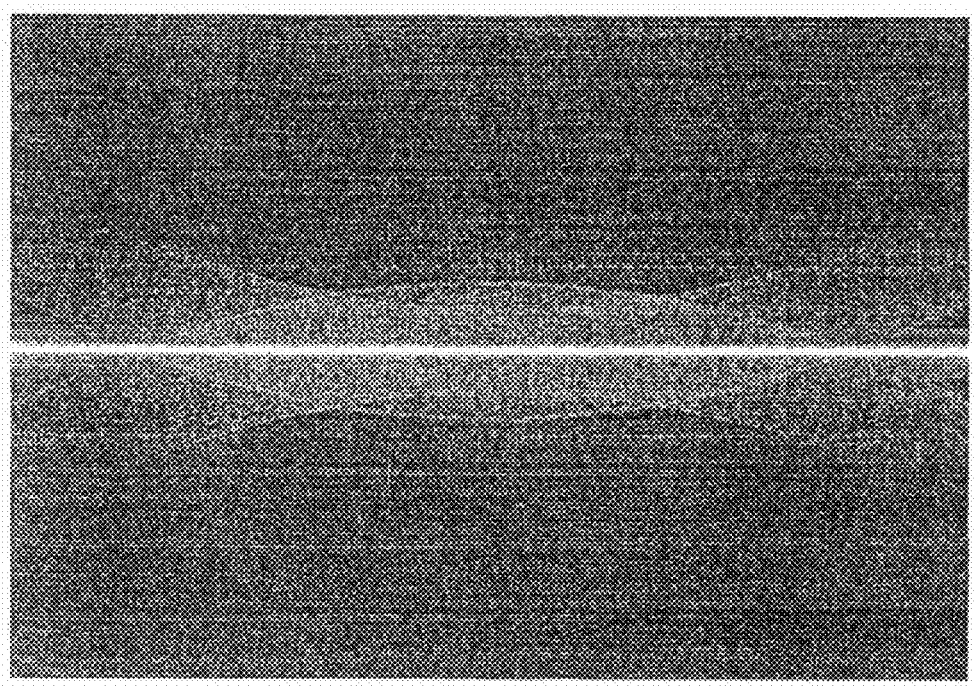
FIGS. 13a and 13b are images of rabbit cornea using the FDOCT system without an EO phase modulator in FIG. 13a and with an EO phase modulator in FIG. 13b.
Figure 13B:
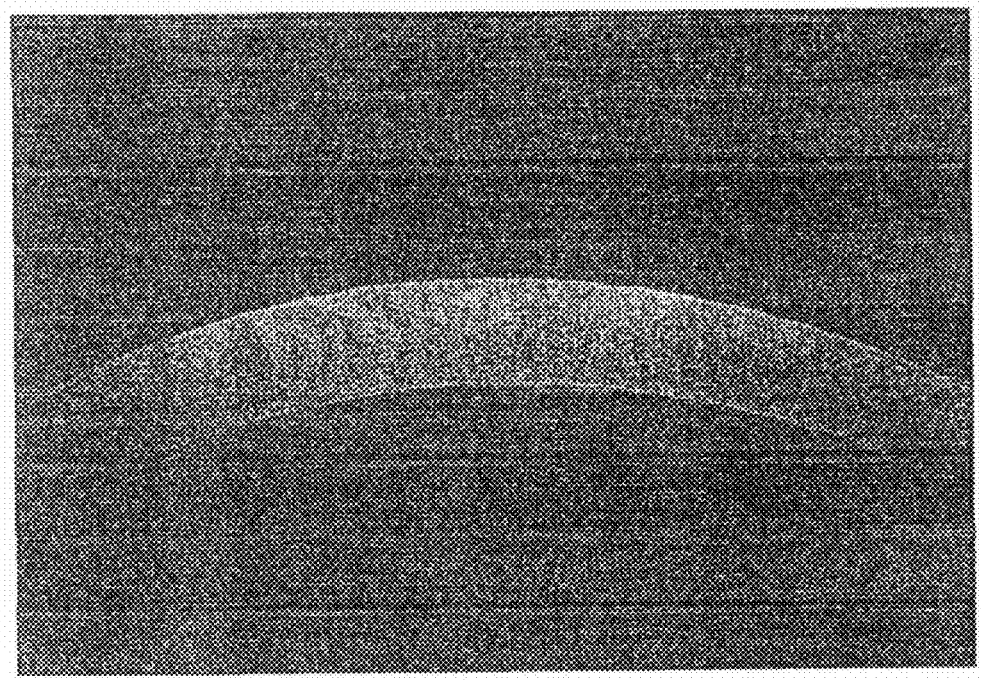

To illustrate the performance of the system, a rabbit cornea was imaged as shown in FIG. 13. The imaged area is 6×4.1 mm with the zero distance difference set in the center of the depth scale. Compared with the image obtained by a conventional FDOCT system without an EO phase modulator, the overlapped mirror images and autocorrelation noise close to the zero position were eliminated using our novel FDOCT system. The system sensitivity was measured with a −57.6 dB partial reflector which was placed 390 μm from the zero position. A sensitivity improvement of 20 dB was obtained as shown in FIG. 14. The imaging range was doubled by removal of the mirror image. The sensitivity measurement showed a 20 dB increase in signal to noise ratio by the elimination of low frequency noises due to DC and autocorrelation terms.

A series of experiments demonstrates the use of FDOCT for characterizing the underlying microcirculation at user-specified locations in highly scattering biological tissues in general, and human skin in particular. Design and development of the instrument for imaging in vivo blood flow is guided here by studies proposed at two levels: (1) in vitro studies with a blood phantom consisting of reconstituted canine blood; and (2) in vivo studies using the chick chorioallantoic membrane (CAM) and rodent skin and mesentery. Experimental results from these models are compared to simulated results from the mathematical modeling. The goal is to determine the quantitative effects of multiple scattering and absorption in both blood and tissue on the FDOCT velocity image. System performance parameters, such as spatial resolution, signal to noise ratio, velocity resolution, and data acquisition time, as well as their interdependence, are studied. Results from these experiments are used to modify and optimize the FDOCT system for clinical applications.

For example, in the case of in vitro studies using reconstituted canine blood an easily available and reproducible in vitro model for studying microvascular blood flow is established and used to investigate the dependence of ODT spectral and temporal interference fringe intensity on various samples, instrumentation, and signal detection parameters. The model also provides data to test and modify various FDOCT image reconstruction procedures. A phantom which simulates microvascular blood flow at user-specified locations in skin is established by injecting a cell suspension into a polyethylene tube submerged in an appropriate concentration of Intralipid. Canine blood is used as the cell suspension because such RBC closely resembles human RBC in size and shape. By using canine RBC, the pronounced forward-scattering properties of human blood will be adequately modeled. Canine RBC will be fixed in glutaraldehyde and suspended in a density-matched medium. This provides a stable sample free from gradual sedimentation and hemolysis which influence prolonged experiments using fresh blood. The use of fixed RBC allows establishment of a stock suspension that can be reproducibly reconstituted at any specified hematocrit. Using the canine blood flow phantom, we investigate the relationship between FDOCT interference fringe intensity and various experimental parameters including incident probe angle, vessel diameter and depth, flow velocity, and RBC and Intralipid concentration. In addition to providing direct insight into the FDOCT detection process. The experimental results are used to test and develop the image reconstruction procedures.

In vivo Studies on Chick Chorioallantoic Membrane (CAM) are used to develop FDOCT for the clinical management of patients where blood flow monitoring is essential. Feasibility studies must be conducted in biological models. The CAM is an established biological model for studying the microcirculation and has been investigated extensively in our laboratory. Because the CAM microvasculature is located in a transparent matrix, direct viewing of the blood vessels throughout their course is possible after the apex of the chick egg shell is removed by opening a 2 cm diameter round window. The extensive three-dimensional nature of the CAM vascular network allows selection of a wide range of horizontal/vertical individual blood vessel orientations and, therefore, Doppler shifts. CAM vessels of different diameters, orientations, and types (vein/artery) will be imaged using FDOCT. Effects of pulsation of blood flow in arteries on the FDOCT image will be investigated. Scattering effects present in skin will be simulated by placing a thin collagen film of known thickness and optical properties on top of the transparent matrix of targeted CAM blood vessel. By changing the thickness of the collagen film, the effect of optical scattering on the FDOCT signal amplitude and frequency can be quantitatively assessed.

In vivo studies on rodent skin and mesentery models are used to introduce the effects of strong optical scattering in biological tissues. These models have been developed and extensively studied using our prototype FDOCT instrument. In vivo blood flow velocity as well as vessel depth and dimension are imaged with spectral FDOCT at predefined sites on the rodent skin and mesentery. The collected data is correlated with histopathological measurements of the depths and physical dimensions of the blood vessels. The experimental procedure is conducted with a number of animals so that statistically significant conclusions can be made. In addition, pedicle and free skin flaps are raised and imaged. Changes in the microvascular circulation due to ischemia, induced by placing a clamp across the base of the skin flap, are assessed. After the clamp is removed, reperfusion of the skin flap after variable ischemia times is also examined. Subsequently, pigs are used to mimic as closely as possible the current surgical practice inasmuch as the animal size allows skin flaps to be constructed having similar dimensions to those used in human reconstructive surgery. Similar ischemia studies are performed on the mesenteric vessels. The effects of pharmacological intervention on the skin and gastrointestinal microcirculation are also evaluated using FDOCT.

In conclusion, the experiments: (1) allow practical "hands on" experience with our FDOCT instrumentation in a preclinical model; and (2) test the ability and limitations of FDOCT to determine accurately blood vessel depths, physical dimensions and flow velocity.

In vivo Imaging of ocular blood flow in the eye provides the single most important and complex sensor with which higher animals and humans perceive the world. Ocular disease and visual functional impairment can have a devastating impact on a patient's quality of life. Because the uninterrupted optical pathway allows direct visual observation of nervous and vascular tissue, the eye provides an important indicator of not only ophthalmologic but also systemic vascular and neurologic disease. Many ophthalmologic diseases may involve disturbances in ocular blood flow, including diabetic retinopathy, low tension glaucoma, anterior ischemic optic neuritis, and macular degeneration. For example, in diabetic retinopathy, retinal blood flow is reduced and the normal autoregulatory capacity is deficient. Ocular hemodynamics are altered in patients with glaucoma and severe loss of visual function has been associated with reduced macular blood flow. Imaging and monitoring of ocular blood flow could have a significant impact in studies of the pathophysiology of these diseases. A galvanometric scanning system is used for imaging in vivo blood flow in ophthalmology. FDOCT imaging optics are integrated with a standard slit-lamp ophthalmoscope so that visual ocular examination can be correlated with high-resolution imaging of ocular blood flow. To demonstrate the ability of FDOCT to image in vivo retinal and optic nerve head blood flow, a rabbit model is initially employed. Tomographic velocity and structural imaging of in vivo retinal and optic nerve head blood flow are recorded. Changes in vessel diameter and flow velocity are imaged after incremental increases of oxygen or addition of vasoactive drugs such as nitrates. The results from the animal model studies are used to further optimize the instrumentation so that it can be used to image in vivo ocular blood flow in human subject. The objective is to make the LAMMP FDOCT available as a resource to study ocular blood flow alterations in ophthalmologic diseases in previously unobtainable detail.

In vivo studies on developmental biology are also envisioned. Noninvasive techniques that can image microcirculation and morphological changes in embryonic development are important for the investigation and understanding of genetic expression, regulation, and control. They are especially valuable in developmental biology research associated with cardiovascular developmental anomalies such as ventricular chamber defects. Currently, ultrasound and confocal microscopy are used for imaging embryonic development. However, ultrasound has a limited resolution (50 μm) and requires the contact of a probe with specimens. Although confocal microscopy provides submicron resolution, their probing depth is limited to less than 1 mm. The high resolution (2-15 μm), noninvasive, and noncontact nature of FDOCT has the potential to become a powerful tool for developmental biology research. In vivo blood microcirculation and morphological changes of several standard biological animal models commonly used in developmental biology will be imaged using the FDOCT developed. Examples are *Xenopus laevis* tadpoles and *Brachydanio rerio* embryos. The measured morphological structure change in different developmental stages will be compared to histology. The FDOCT system is modified and optimized so that biologists can routinely apply this technology to study developmental biology such as embrogenesis.

Clinical applications of FDOCT require a dedicated, portable, high speed FDOCT instrument. Once the high speed spectral FDOCT is built and tested in in vitro and in vivo models, this LAMMP FDOCT system is available for sharing and collaborative projects with the biomedical community. FDOCT has broad implications for the clinical management of patients where blood flow monitoring is essential. A number of collaborative clinical investigations are carried out including: 1) evaluation of port wine stain laser therapy efficiency, 2) monitoring intraluminal blood flow during photodynamic therapy, 3) determination of burn depth; and 4) evaluating viability of skin flap in microsurgery. Because FDOCT technology is relatively new with the first in vitro flow imaging published in January 1997, we expect many more collaborative clinical studies to be developed as awareness of this technology increases in the biomedical community.

Many alterations and modifications may be made by those having ordinary skill in the art without departing from the spirit and scope of the invention. For example, throughout this specification and claims, and particularly in the equations, it is always possible to equivalently or interchangeably express the quantities as functions of either z or τ by means of the equality, $z=c\,\tau$, or as either functions of v or k by means of the equality, $v=c\,k/2\pi$, where c is the speed of light in a vacuum. $P(v,t)$, $\Gamma(t)$ and $I(k)$ are interference signals, and $\tilde{\Gamma}(v)$ and $\tilde{I}(k)$ are complex interference signals.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for tomographic imaging of a sample comprising:

providing light from a swept frequency source of at least partially coherent radiation to an interferometer;

phase modulating the radiation in the interferometer to produce a phase modulated signal at a modulation frequency combined with a carrier signal at a frequency sufficient to separate the negative and positive frequency terms of an interference fringe signal from each other and from the low frequency noise which is not affected by the carrier frequency;

detecting the interference fringe signal of the radiation backscattered from the sample into the interferometer to obtain a spectral signal;

transforming the spectral signal of the detected backscattered interference fringes to obtain a location dependent signal; and generating a displayable tomographic image of fluid flow in the data window and of the structure of the sample in the data window from the location dependent signal.

2. The method of claim 1 where detecting the interference fringes signal of the radiation backscattered from the sample and transforming the spectral signal comprises measuring the time variation of spectral interference fringe intensity ($P_{ODT}(v, t)$) to determine the positions of scattering constituents along the beam propagation axes of the interferometer by an inverse Fourier transformation of the optical spectrum and to determine the velocity of the moving particles from the oscillation frequency of the optical spectrum in the time domain at each pixel in the data window.

3. The method of claim 2 where measuring the time variation of spectral interference fringe intensity ($P_{ODT}(v, t)$) comprises simultaneously acquiring position and velocity information over $N_z$ pixels in the direction of the scan depth.

4. The method of claim 1 where detecting interference fringe signal of the radiation backscattered from the sample comprises determining both the phase and amplitude of the interference fringe by digital Fourier transformation of P(v, t) to obtain the complex valued analytic fringe signal $\tilde{\Gamma}(\tau)$ and then determining the Doppler shift and variance from the complex valued analytic fringe signal $\tilde{\Gamma}(\tau)$ by either phase resolved signal processing or wavelet analysis, where determining the Doppler shift and variance from the complex valued analytic fringe signal $\tilde{\Gamma}(\tau)$ by either phase resolved signal processing comprises determining the Doppler frequency shift (fn) and standard deviation ($\sigma_n$) values at the nth pixel from the spectral data:

$$f_n = \frac{1}{2\pi T}\tan^{-1}\left(\frac{\text{Im}\left[\sum_{m=(n-1)M}^{nM}\sum_{j=1}^{4}\tilde{\Gamma}_j(\tau_m)\tilde{\Gamma}^*_{j+1}(\tau_m)\right]}{\text{Re}\left[\sum_{m=(n-1)M}^{nM}\sum_{j=1}^{4}\tilde{\Gamma}_j(\tau_m)\tilde{\Gamma}^*_{j+1}(\tau_m)\right]}\right) \quad (16)$$

-continued $$\sigma^2 = \frac{1}{2\pi^2 T^2}\left(1 - \frac{\left|\sum_{m=(n-1)M}^{nM}\sum_{j=1}^{4}\tilde{\Gamma}_j(\tau_m)\tilde{\Gamma}^*_{j+1}(\tau_m)\right|}{\frac{1}{2}\sum_{m=(n-1)M}^{nM}\sum_{j=1}^{4}\left[\begin{array}{c}\tilde{\Gamma}_j(\tau_m)\tilde{\Gamma}^*_j(\tau_m) + \\ \tilde{\Gamma}_{j+1}(\tau_m)\tilde{\Gamma}^*_{j+1}(\tau_m)\end{array}\right]}\right) \quad (17)$$

where $\tilde{\Gamma}_j(\tau_m)$ and $\tilde{\Gamma}^*_j(\tau m)$ are the complex signals corresponding to the jth fringe signal and its conjugate, respectively, $\tilde{\Gamma}_{j+1}(\tau_m)$ and $\tilde{\Gamma}^*_{j+1}(\tau_m)$ are the complex signals corresponding to the next fringe signal and its conjugate, respectively, T is the time duration between sequential fringe data, and M is an even number that denotes the window size in the axial direction for each pixel.

5. The method of claim 1 where phase modulating the radiation in the interferometer at a modulation frequency comprises generating a stable carrier frequency at approximately 1 MHz for elimination of the mirror image and low frequency noise using a phase modulator.

6. The method of claim 5 further comprising matching dispersion caused by the phase modulator with a rapid scanning optical delay line with a fixed mirror to compensate for the group velocity dispersion.

7. The method of claim 1 where transforming the spectral signal of the detected backscattered interference fringes comprises generating a complex analytical depth encoded signal $\tilde{S}(z)$ using a data processing algorithm to convert a time fringe signal, $\Gamma(t)$, to $G(v)$ in frequency space by digitally fast Fourier transforming the time fringe signal, $\Gamma(t)$, multiplying it by the Heaviside function, bandpass filtering the result to remove the low frequency and DC noises, demodulating the result to shift the center frequency of the filtered interference term to zero frequency, converting the resulting frequency fringe signal back to time space by inverse fast Fourier transforming the result, canceling the distortion originating from the nonlinearities in the wave number function $k(t)$ by remapping the result from uniform time to uniform wave number space based on the function of $k(t)$ which is determined by the dynamic calibration of the swept wave number function, and fast Fourier transforming the result in $k$ space to result in the complex depth encoded interference fringe signal $\tilde{S}(z)=A(z)e^{i\phi(z)}$ which contains both the amplitude A(z) and phase $\phi(z)$ terms.

8. The method of claim 1 where generating a stable carrier frequency for elimination of the mirror image and low frequency noise using a phase modulator comprises generating a predetermined carrier frequency so that the negative and positive terms of the Fourier transformed interference signal are separated from each other and from the low frequency noise which is not affected by the carrier frequency, but which low frequency noise is due to DC and autocorrelation terms, and where generating a tomographic image comprises constructing the tomographic image from only one of the negative or positive terms of the Fourier transformed interference fringe signal.

9. An apparatus for tomographic imaging of a sample comprising:

an interferometer;

a swept frequency source of at least partially coherent radiation coupled to the interferometer;

a phase modulator of the radiation in the interferometer operating at a stable modulation frequency combined with a carrier signal at a carrier frequency sufficient to separate the negative and positive frequency terms of an interference fringe signal from each other and from the low frequency noise which is not affected by the carrier frequency, the phase modulator being in optical circuit in the interferometer;

a detector of interference fringes of the radiation backscattered from the sample into the interferometer, where the detector obtains a spectral signal and is coupled to the interferometer;

circuit means coupled to the detector for transforming the spectral signal of the detected backscattered interference fringes to obtain a location dependent signal, including the Doppler shift and variance, at each pixel location in a window; and a generator to produce a displayable tomographic image of the fluid flow in the data window and of the structure of the scanned sample in the data window from the location dependent signal coupled from the circuit means.

10. The apparatus of claim 9 where the circuit means for transforming the spectral signal comprises a circuit means for generating a spectrogram for each pixel location in the data window, frequency filtering the generated spectrogram for each pixel location in the data window and generating a structural F-OCT image from the filtered spectrogram.

11. The apparatus of claim 9 where the detector of interference fringes of the radiation backscattered from the sample into the interferometer to obtain a spectral signal comprises an optical spectrum analyzer coupled to the interferometer, the optical spectrum analyzer for acquiring data for F-OCT structural and velocity images in parallel to measure time variation of spectral interference fringe intensity ($P_{ODT}(v, t)$).

12. The apparatus of claim 9 where the detector of interference fringes of the radiation backscattered from the sample and the circuit means for transforming the spectral signal comprises a circuit means for measuring the time variation of spectral interference fringe intensity ($P_{ODT}(v, t)$) to determine the positions of scattering constituents along the beam propagation axes of the interferometer by an inverse Fourier transformation of the optical spectrum and to determine the velocity of the moving particles from the oscillation frequency of the optical spectrum in the time domain at each pixel in the data window.

13. The apparatus of claim 12 where the circuit means for measuring the time variation of spectral interference fringe intensity ($P_{ODT}(v, t)$) comprises a circuit means for simultaneously acquiring position and velocity information over $N_z$ pixels in the direction of the scan depth.

14. The apparatus of claim 9 where the detector of interference fringes of the radiation backscattered from the sample comprises a circuit means for determining both the phase and amplitude of the interference fringe by digital Fourier transformation of P(v, t) to obtain the complex valued analytic fringe signal $\tilde{\Gamma}(\tau)$, and then determining the Doppler shift and variance from the complex valued analytic fringe signal $\tilde{\Gamma}(\tau)$ by either phase resolved signal processing or wavelet analysis.

15. The apparatus of claim 14 where the circuit means for determining the Doppler shift and variance from the complex valued analytic fringe signal $\tilde{\Gamma}(\tau)$ by either phase resolved signal processing comprises a circuit means for determining the Doppler frequency shift (fn) and standard deviation ($\sigma_n$) values at the nth pixel from the spectral data:

$$f_n = \frac{1}{2\pi T} \tan^{-1} \left( \frac{\mathrm{Im}\left[ \sum_{m=(n-1)M}^{nM} \sum_{j=1}^{4} \tilde{\Gamma}_j(\tau_m)\tilde{\Gamma}^*_{j+1}(\tau_m) \right]}{\mathrm{Re}\left[ \sum_{m=(n-1)M}^{nM} \sum_{j=1}^{4} \tilde{\Gamma}_j(\tau_m)\tilde{\Gamma}^*_{j+1}(\tau_m) \right]} \right) \quad (16)$$

$$\sigma^2 = \frac{1}{2\pi^2 T^2}\left( 1 - \frac{\left| \sum_{m=(n-1)M}^{nM} \sum_{j=1}^{4} \tilde{\Gamma}_j(\tau_m)\tilde{\Gamma}^*_{j+1}(\tau_m) \right|}{\frac{1}{2}\sum_{m=(n-1)M}^{nM} \sum_{j=1}^{4} \left[ \begin{array}{c} \tilde{\Gamma}_j(\tau_m)\tilde{\Gamma}^*_j(\tau_m) + \\ \tilde{\Gamma}_{j+1}(\tau_m)\tilde{\Gamma}^*_{j+1}(\tau_m) \end{array} \right]} \right) \quad (17)$$

where $\tilde{\Gamma}_j(\tau_m)$ and $\tilde{\Gamma}^*_j(\tau_m)$ are the complex signals corresponding to the jth fringe signal and its conjugate, respectively, $\tilde{\Gamma}_{j+1}(\tau_m)$ and $\tilde{\Gamma}^*_{j+1}(\tau_m)$ are complex signals corresponding to the next fringe signal and its conjugate, respectively, T is the time duration between sequential fringe data, and M is an even number that denotes the window size in the axial direction for each pixel.

16. The apparatus of claim 15 where the generator of the tomographic image comprises a circuit means for averaging the calculated Doppler frequency shifts and standard deviation values to obtain the Doppler shift and variance images.

17. The apparatus of claim 9 where the circuit means for detecting interference fringes of the radiation backscattered from the sample into the interferometer to obtain a spectral signal comprises a photodetector coupled to the at the interferometer for acquiring data for F-OCT structural and velocity images in parallel to measure time variation of spectral interference fringe intensity ($P_{ODT}(v, t)$).

18. The apparatus of claim 9 where the phase modulator in the interferometer generates a stable carrier frequency for elimination of the mirror image and low frequency noise.

19. The apparatus of claim 18 further comprising a rapid scanning optical delay line with a fixed mirror to match dispersion caused by the phase modulator to compensate for the group velocity dispersion.

20. The apparatus of claim 9 where the circuit means for transforming the spectral signal of the detected backscattered interference fringes comprises a data processing circuit means for generating a complex analytical depth encoded signal $\tilde{S}(z)$ to convert a time fringe signal $\Gamma(t)$ to G(v) in frequency space by digitally fast Fourier transforming the time fringe signal, $\Gamma(t)$, multiplying it by the Heaviside function, bandpass filtering the result to remove the low frequency and DC noises, demodulating the result to shift the center frequency of the filtered interference term to zero frequency, converting the resulting frequency fringe signal back to time space by inverse fast Fourier transforming the result, canceling the distortion originating from the nonlinearities in the wave number function k(t) by remapping the result from uniform time to uniform wave number space based on the function of k(t) which is determined by the dynamic calibration of the swept wave number function, and fast Fourier transforming the result in k space to result in the complex depth encoded fringe signal $\tilde{S}(z)=A(z)e^{i\phi(z)}$ which contains both the amplitude A(z) and phase $\phi(z)$ terms, and for reconstructing a structure image from the amplitude information, for reconstructing Doppler mean frequency and Doppler standard deviation images by comparing the phase term between sequential scans, and for reconstructing a birefringence image from the phase and amplitude information of the signals from both polarizations of the complex depth encoded fringe signals from two perpendicular polarization-detection channels.

21. The apparatus of claim 9 where the phase modulator for generating a stable carrier frequency for elimination of the mirror image and low frequency noise generates a predetermined carrier frequency so that the negative and positive terms of the Fourier transformed interference signal are separated from each other and from the low frequency noise which is not affected by the carrier frequency, but due to DC and autocorrelation terms, and where the generator to produce a tomographic image comprises means for generating a tomographic image comprises constructing the tomographic image from only one of the negative or positive terms of the Fourier interferer signal.

* * * * *